(12) United States Patent
Anderson et al.

(10) Patent No.: US 11,358,947 B2
(45) Date of Patent: Jun. 14, 2022

(54) SUBSTITUTED 2-ACYLAMINO-CYCLOALKYLTHIOPHENE-3-CARBOXYLIC ACID ARYLAMIDES AS INHIBITORS OF CALCIUM-ACTIVATED CHLORIDE CHANNEL TMEM16A

(71) Applicants: THE REGENTS OF THE UNIVERSITY OF CALIFORNIA, Oakland, CA (US); Marc O. Anderson, San Francisco, CA (US)

(72) Inventors: Marc O. Anderson, San Francisco, CA (US); Alan S. Verkman, San Francisco, CA (US); Puay Wah Phuan, San Francisco, CA (US)

(73) Assignees: The Regents of the University of California, Oakland, CA (US); Marc O. Anderson, San Francisco, CA (US)

( * ) Notice: Subject to any disclaimer, the term of this patent is extended or adjusted under 35 U.S.C. 154(b) by 0 days.

(21) Appl. No.: 16/606,200

(22) PCT Filed: Apr. 17, 2018

(86) PCT No.: PCT/US2018/028039
§ 371 (c)(1),
(2) Date: Oct. 17, 2019

(87) PCT Pub. No.: WO2018/195127
PCT Pub. Date: Oct. 25, 2018

(65) Prior Publication Data
US 2020/0123128 A1    Apr. 23, 2020

Related U.S. Application Data

(60) Provisional application No. 62/486,367, filed on Apr. 17, 2017.

(51) Int. Cl.
| | | |
|---|---|---|
| *C07D 333/80* | (2006.01) | |
| *A61P 9/12* | (2006.01) | |
| *A61P 35/00* | (2006.01) | |
| *C07D 333/68* | (2006.01) | |
| *C07D 333/78* | (2006.01) | |
| *C07D 495/04* | (2006.01) | |

(52) U.S. Cl.
CPC .............. *C07D 333/80* (2013.01); *A61P 9/12* (2018.01); *A61P 35/00* (2018.01); *C07D 333/68* (2013.01); *C07D 333/78* (2013.01); *C07D 495/04* (2013.01)

(58) Field of Classification Search
CPC .................................................. C07D 333/80
See application file for complete search history.

(56) References Cited

U.S. PATENT DOCUMENTS

2011/0015239 A1    1/2011    Verkman et al.

FOREIGN PATENT DOCUMENTS

| JP | 2004-137185 A | 5/2004 | |
|---|---|---|---|
| WO | WO-2006026619 A2 * | 3/2006 | ........... A61K 31/381 |
| WO | 2006/044826 A2 | 4/2006 | |
| WO | WO-2006044826 A2 * | 4/2006 | ........... C07D 495/04 |

OTHER PUBLICATIONS

Chemical Abstracts Registry No. 183129-01-3, indexed in the Registry file on STN CAS Online Nov. 14, 1996. (Year: 1996).*
PubChem CID 991345, National Center for Biotechnology Information. PubChem Compound Summary for CID 991345. https://pubchem.ncbi.nlm.nih.gov/compound/991345. Accessed Oct. 7, 2020, create date Jul. 9, 2005. (Year: 2005).*
PubChem CID 1047339 {National Center for Biotechnology Information. PubChem Compound Summary for CID 1047339. https://pubchem.ncbi.nlm.nih.gov/compound/1047339. Accessed Oct. 8, 2020, create date Jul. 10, 2005. (Year: 2005).*
Davis et al., "Identification of Novel *Plasmodium falciparum* Hexokinase Inhibitors with Antiparasitic Activity" *Antimicrobial Agents and Chemotherapy* 60(10):6023-6033, 2016.
Extended European Search Report, dated Nov. 13, 2020, for European Application No. 18788374.9, 8 pages.
International Search Report and Written Opinion, dated Aug. 10, 2018, for International Application No. PCT/US2018/028039, 10 pages.
Oh et al., "Synthesis and biological evaluation of 2-acetamidothiophene-3-carboxamide derivatives against *Leishmania donovani*," *Med. Chem. Commun.* 5:142-146, 2014.
Pubchem, CID 1047339, National Center for Biotechnology Information, PubChem Compound Summary for CID 1047339, https://pubchem.ncbi.nlm.nih.gov/compound/1047339, 2005 (13 pages).

* cited by examiner

*Primary Examiner* — Laura L Stockton
(74) *Attorney, Agent, or Firm* — Seed IP Law Group LLP

(57) ABSTRACT

Provided herein are inhibitors of transmembrane protein 16A (TMEM 16A), a $Ca^{2+}$-activated $Cl^-$ channel expressed widely in mammalian epithelia, as well as in vascular smooth muscle and some tumors and electrically excitable cells. TMEM16A inhibitors have potential utility for treatment or management of disorders of epithelial fluid and mucus secretion, hypertension, some cancers, pain, and other diseases.

9 Claims, 5 Drawing Sheets

SUBSTITUTED 2-ACYLAMINO-CYCLOALKYLTHIOPHENE-3-CARBOXYLIC ACID ARYLAMIDES AS INHIBITORS OF CALCIUM-ACTIVATED CHLORIDE CHANNEL TMEM16A

CROSS REFERENCE TO RELATED APPLICATION

This application claims the benefit under 35 U.S.C. § 119(e) to U.S. Provisional Application 62/486,367 filed Apr. 17, 2017, which application is incorporated by reference herein in its entirety.

STATEMENT OF GOVERNMENT INTEREST

This invention was made with government support under grant nos. R15 GM102874, P30 DK072517 and R01 DK101373 awarded by the National Institutes of Health. The government has certain rights in the invention.

BACKGROUND

Technical Field

This disclosure is related to inhibitors of chloride conductance via calcium-activated chloride channels and use thereof.

Description of the Related Art

TMEM16A (also known as anoctamin1, ANO1, DOG1, ORAOV2, TAOS-2) is a $Ca^{2+}$-activated $Cl^-$ channel (CaCC) that is expressed widely in mammalian tissues, including secretory epithelial cells, smooth muscle cells, interstitial cells of Cajal, and nociceptive neurons. (See Pedemonte, N. et al., *Physical Rev* 2014, 94, (2), 419-59; Picollo, A. et al., *J Mol Biol* 2015, 427, (1), 94-105; Oh, U. et al., *Pflugers Arch* 2016, 468, (3), 443-53.) TMEM16A is overexpressed in some human cancers in which its expression correlates with tumor grade. (See Qu, Z. et al., *Cancer Med* 2014, 3, (3), 453-61; Wanitchakool, P. et al., *Philos Trans R Soc Lund B Biol Sci* 2014, 369, (1638), 20130096.) TMEM16A was also reported as a biomarker for gastrointestinal stromal and esophageal tumors and TMEM16A expression is associated with good prognosis in PR-positive or HER2-negative breast cancer patients following tamoxifen treatment. (See Li, Q. et al., *Oncotarget* 2016; Shang, L. et al., *Oncotarget* 2016, 7, (17), 24374-82; Wu, H. et al., *PLoS One* 2015, 10, (5), e0126128,) Studies in TMEM16A knockout mice have suggested its involvement in tracheal development and mucociliary clearance, with knockout mice showing airway mucus accumulation. (See Huang, F. et al., *Proc Natl Acad Sci USA* 2009, 106, (50), 21413-8; Rock, J. R. et al., *Dev Biol* 2008, 321, (1), 141-9; Ousingsawat, J. et al., *J Biol Chem* 2009, 284, (42), 28698-703; Rock, J. R. et al., *J Biol Chem* 2009, 284, (22), 14875-80.) TMEM16A knockout or knockdown is associated with diminished rhythmic contraction of gastric smooth muscle cells, defective protein reabsorption in kidney proximal tubule, and attenuated pain response. (See Huang, F. et al., *Proc Natl Acad Sci USA* 2009, 106, (50), 21413-8; Faria, D. et al., *Kidney Int* 2014, 85, (6), 1369-81; Lee, B. et al., *Mol Pain* 2014, 10, 5.) TMEM16A knockout mice also manifest reduced blood pressure and a decreased hypertensive response following vasoconstrictor treatment. (See Heinze, C. et al., *J Clin Invest* 2014, 124, (2), 675-86.) TMEM16A knockdown in spontaneously hypertensive rats reduced blood pressure and prevented the development of hypertension. (See Wang, B. et al., *J Mol Cell Cardiol* 2015, 82, 22-32.)

TMEM16A contains eight putative transmembrane domains with intracellular $NH_2$ and COOH termini, and two calmodulin binding domains. (See Pedemonte, N. et al., *Physiol Rev* 2014, 94, (2), 419-59; Picollo, A. et al., *J Mol Biol* 2015, 427, (1), 94-105.) Putative $Ca^{2+}$ binding sites are located at E702 and E705. (See Yu, K. et al., *Circ Res* 2012, 110, (7), 990-9.) The TMEM16A protein appears to be structured as a homodimer. (See Fallah, G. et al., *Mol Cell Proteomics* 2011, 10, (2), M110 004697; Sheridan, J. T. et al., *J Biol Chem* 2011, 286, (2), 1381-8.) TMEM16A is expressed in multiple splice variants that have variable sensitivity to cytosolic $Ca^{2+}$. (See Tian, Y. et al., *Faseb J* 2011, 25, (3), 1058-68; Tian, Y. et al., *J Cell Sci* 2012, 125, (Pt 21), 4991-8.) An X-ray crystal structure (3.4 Å resolution) was recently solved of a fungal TMEM16 isoform with $Ca^{2+}$-activated lipid scramblase activity (nhTMEM16) having 39-42% homology to mammalian TMEM16A. (See Brunner, J. D. et al., *Nature* 2014, 516, (7530), 207-12.)

Pharmacological inhibition of TMEM16A has been proposed to be of utility for inflammatory and reactive airways diseases and hypertension, and perhaps for pain and cancer. (See Pedemonte, N. et al., *Physiol Rev* 2014, 94, (2), 419-59; Oh, U. et al., *Pflugers Arch* 2016, 468, (3), 443-53; Qu, Z. et al., *Cancer Med* 2014, 3, (3), 453-61; Jia, L. et al., *PLoS One* 2015, 10, (8), e0136584.) TMEM16A activation has been considered as a therapeutic strategy to treat cystic fibrosis, gastrointestinal hypomotility and salivary gland hypofunction. (See Mall, M. A. et al., *J Cyst Fibres* 2015, 14, (5), 561-70; Sondo, E. et al., *Int J Biochem Cell Biol* 2014, 52, 73-6; Namkung, W. et al., *Faseb J* 2011, 25, (11), 4048-4062.) TMEM16A has recently been proposed as a target in chronic inflammatory disease. (See Sala-Rabanal, M. et al., *Mediators Inflamm* 2015, 2015, 497387.)

Non-selective CaCC inhibitors, which inhibit TMEM16A as well as non-TMEM16A (as yet unidentified) CaCCs have been identified by high-throughput screening. (See De La Fuente, R. et al., *Mol Pharmacol* 2008, 73, (3), 758-68.) TMEM16A-selective inhibitors have been identified from functional screens using TMEM16A-transfected cells, which include aminothiazoles linked to a di-substituted pyrimidine (T16A$_{inh}$-A01). (See Namkung, W. et al., *J Biol Chem* 2011, 286, (3), 2365-74; Piechowicz, K. A. et al., *J Enzyme Inhib Med Chem.* 2016, 1-7.) Subsequently reported TMEM16A inhibitors include N-((4-methoxy)-2-naphthyl)-5-nitroanthranilic acid (MONNA), and the acyl hydrazone Ani-9. (See Oh, S. J. et al., *Mol Pharmacol* 2013, 84, (5), 726-35; Seo, Y. et al., *PLoS One* 2016, 11, (5), e0155771.) (FIG. 1) T16A$_{inh}$-A01 has been shown to block $Ca^{2+}$-activated $Cl^-$ currents in vascular smooth muscle cells, and relax mouse and human blood vessels. (See Davis, A. J., *Br J Pharmacal* 2013, 168, (3), 773-84.) T16A$_{inh}$-A01 has also been used to prevent serotonin-induced contractile response in pulmonary arteries of chronic hypoxic rats, a model of pulmonary hypertension and to reverse EGF-induced increases in CaCC currents in T84 colonic epithelial cells. (See Sun, H., *J Physiol* 2012, 590, (Pt 15), 3507-21; Mroz, M. S., *J Physiol* 2012, 590, (Pt 8), 1907-20.) Recently, T16A$_{inh}$-A01 was also shown to attenuate angiotensin II-induced cerebral vasoconstriction in rat basilar arteries, supporting the role of TMEM16A in hypertension. (See Li, R. S., *Mol Med Rep* 2016, 13, (4), 3691-9.) In another recent study T16A$_{inh}$-A01 inhibited cell proliferation and caused apoptosis in TMEM16A-expressing PC-3 and CFPAC-1 cancer cells, but not in A549 cells that do not express TMEM16A. (See Seo, Y., *PLoS One* 2015, 10, (7), e0133656.)

BRIEF SUMMARY

Provided herein are 2-acylamino-cycloalkylthiophene-3-carboxylic acid arylamide (AACT) class of TMEM16A inhibitors with substantially improved inhibition potency and metabolic stability than currently known inhibitors.

One embodiment provides a compound having the structure represented by Formula I:

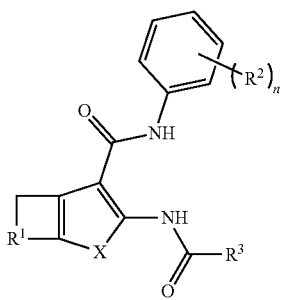

(I)

or a pharmaceutically acceptable salt, isotopic form, stereoisomer or prodrug thereof,
wherein:
n is 1, 2, 3 or 4;
X is S, O, or NR;
R is hydrogen or $C_1$-$C_6$ alkyl;
$R^1$ is optionally substituted $C_1$-$C_6$ alkylene or optionally substituted $C_1$-$C_5$ heteroalkylene;
each $R^2$ is the same or different and independently hydrogen, halo, $C_1$-$C_6$ alkyl, $C_1$-$C_6$ alkoxy, $C_1$-$C_6$ haloalkyl, or $C_1$-$C_6$; haloalkoxy; and
$R^3$ is $C_1$-$C_6$ alkyl, or $C_1$-$C_6$ haloalkyl, with the proviso that the compound of Formula (I) is not 2-(2,2,2-Trifluoroacetylamino)-5,6,1,8-tetrahydro4H-cyclohepta[b]thiophene-3-carboxylic acid o-tolylamide.

Another related embodiment provides a pharmaceutical composition comprising a physiologically acceptable excipient and a compound of Formula (1).

Other embodiments provide a use of a composition or a compound of Formula (1) or any one of the substructures as represented by Formulae (I-1)-(I-14), for treating a condition, disease, or disorder associated with abnormally increased chloride ion secretion from a cell. Certain embodiments provide a use of a composition or a compound of Formula (I) or any one of the substructures as represented by Formulae (I-1)-(I-14), for reducing or managing pain, or for treating cancer, or for treating hypertension.

Another embodiment provides use of a composition or a compound of Formula (I) or any one of the substructures as represented by Formulae (I-1)-(I-14), for the manufacture of a medicament for treating a condition, disease, or disorder associated with abnormally increased chloride ion secretion from a cell.

These and other aspects of the invention, as well as advantages related to the same, will be apparent upon reference to the following detailed description.

BRIEF DESCRIPTION OF THE SEVERAL VIEWS OF THE DRAWINGS

FIG. 5A shows the concentration-dependent inhibition of SW-480 cell proliferation by compounds according to certain embodiments; FIG. 5B shows the structures of compounds of 5A.

DETAILED DESCRIPTION

Figure 1:
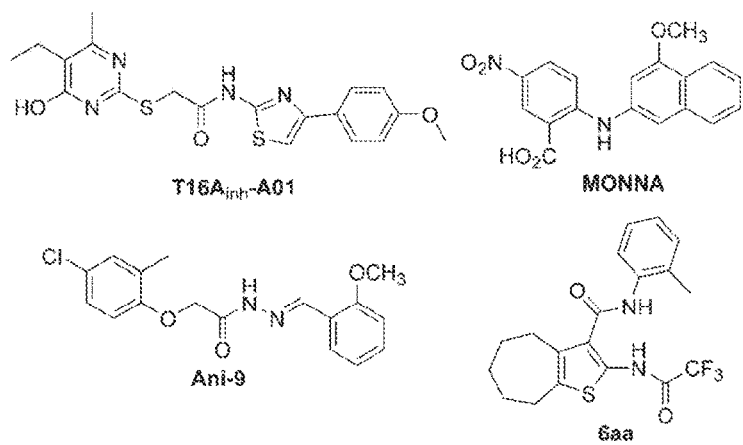
FIG. 1 shows structures of T16A$_{inh}$-A01, MONNA, Ani-9, which are known TMEM16A inhibitors; as well as the structure of a cycloalkylthiophene inhibitor (6aa), the TMEM16A inhibition of which is disclosed herein.

A high-throughput screening assay was previously developed to identify small molecule inhibitors of TMEM16A. (See Namkung, W. et al., *Faseb J* 2011, 25, (11), 4048-4062.) The screen utilized FRT cells that were stably transfected with human TMEM16A and the iodide-sensitive fluorescent protein YFP-H148Q/1152L/F46L. The assay involved addition of test compounds to the cells for 10 min in a physiological chloride-containing solution, followed by addition of an iodide solution containing ATP. TMEM16A-facilitated iodide influx was determined from the initial time course of decreasing YFP fluorescence. TMEM16A inhibitors reduce iodide influx, resulting a reduced rate of decreasing fluorescence, Several classes of inhibitors with micromolar potency, including T16A$_{inh}$-A01, were discovered. (See Namkung, W. et al., *Faseb J* 2011, 25, (11), 4048-4062; Piechowicz, K. A. et al., *J Enzyme Inhib Med Chem* 2016, 1-7.) Screening of 50,000 drug-like synthetic small molecules identified 2-acylamino-cycloalkylthiophene-3-carboxylic acid arylamide (AACT) 6aa with IC$_{50}$ ~0.42 μM.

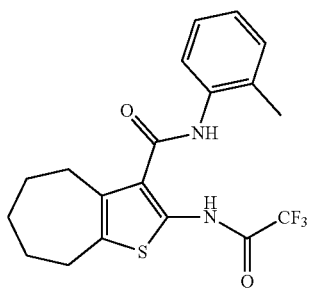

The only other reported biological activity AACTs is inhibition of the protozoan parasite *Leishmania donovani* ($EC_{50}$=6.4 μM), with no cytotoxicity seen against human macrophages ($CC_{50}$>50 μM). (See Oh, S., *MedChemComm* 2014, 5, (2), 142-146.).

Provided herein are 2-acylamino-cycloalkylthiophene-3-carboxylic acid arylamide (AACT) derivatives, which are potent TMEM16A inhibitors.

One embodiment provides a compound having the structure represented by Formula I:

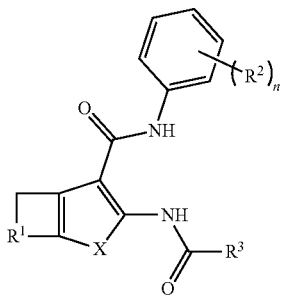

(I)

or a pharmaceutically acceptable salt, isotopic form, stereoisomer or prodrug thereof, wherein:

n is 1, 2, 3 or 4;

X is S, O, or NR;

R is hydrogen or $C_1$-$C_6$ alkyl;

$R^1$ is optionally substituted $C_1$-$C_6$ alkylene or optionally substituted $C_1$-$C_5$ heteroalkylene;

each $R^2$ is the same or different and independently hydrogen, halo, $C_1$-$C_6$ alkyl, $C_1$-$C_6$ alkoxy, $C_1$-$C_6$ haloalkyl, or $C_1$-$C_6$ haloalkoxy; and $R^3$ is $C_1$-$C_6$ alkyl, or $C_1$-$C_6$ haloalkyl, with the proviso that the compound of Formula (I) is not 2-(2,2,2-Trifluoroacetylamino)-5,6,7,8-tetrahydro-4H-cyclohepta[b]thiophene-3-carboxylic acid o-tolylamide.

More specific embodiments provide a compound having one of the following structures Formula (I-1), Formula (I'-1), Formula (I-2), Formula (I-3), or Formula (I-4):

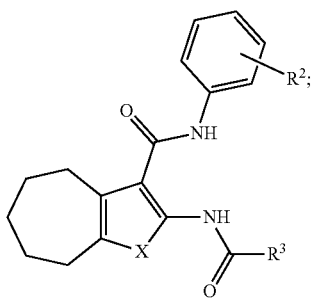

Formula (I-1)

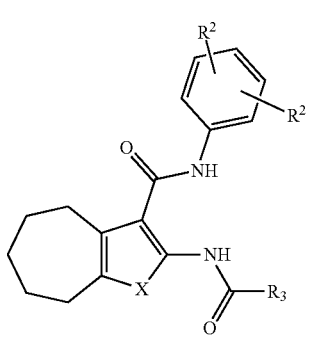

Formula (I'-1)

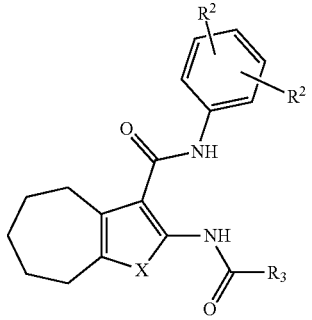

Formula (I-2)

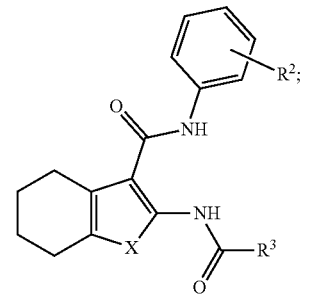

Formula (I-3)

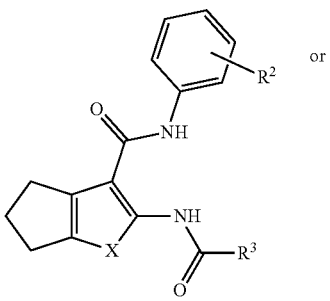

or

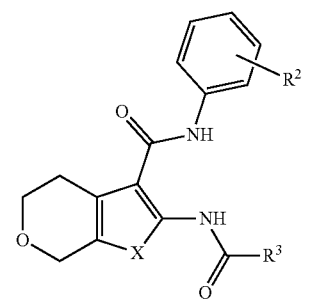

Formula (I-4)

wherein:

X is S, O, or NH;

each $R^2$ is independently hydrogen, halo, $C_1$-$C_6$ alkyl, $C_1$-$C_6$ alkoxy, $C_1$-$C_6$ haloalkyl, or $C_1$-$C_6$ haloalkoxy; and $R^3$ is $C_1$-$C_6$ alkyl, or $C_1$-$C_6$ haloalkyl.

In preferred embodiments, X is S in any one of Formulae (I-1), (I'-1), (I-2), (I-3) and (I-4); and the compounds are

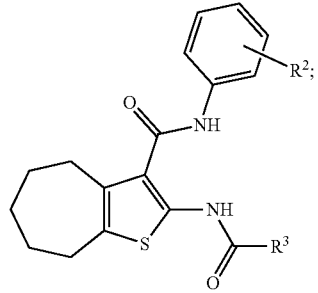

(I-1a)

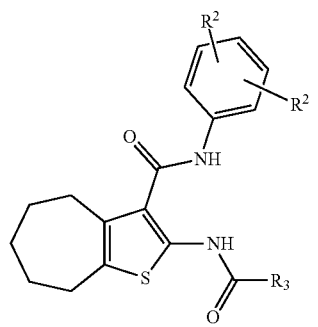

(I'-1a)

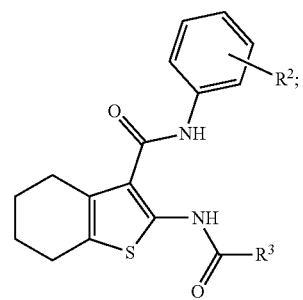

(I-2a)

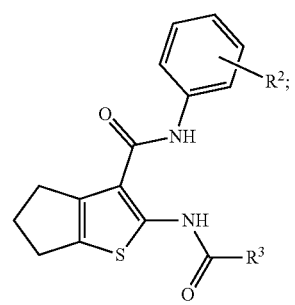

(I-3a)

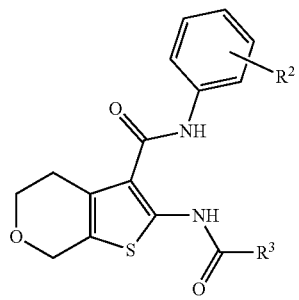

(I-4a)

Further embodiments provide a compound having one of the following structures Formula (I-5), Formula (I-6) or Formula (I'-6):

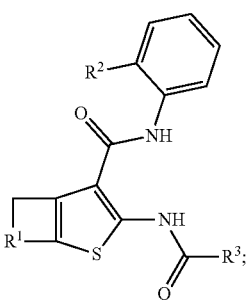

Formula (I-5)

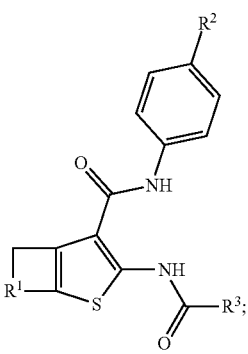

Formula (I-6)

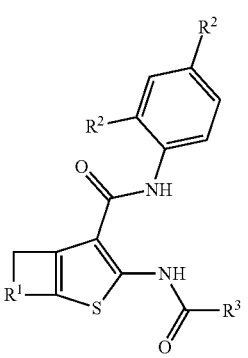

Formula (I'-6)

wherein:
R¹ is optionally substituted $C_1$-$C_6$ alkylene or optionally substituted $C_1$-$C_5$ heteroalkylene;
each R² is independently hydrogen, halo, $C_1$-$C_6$ alkyl, $C_1$-$C_6$ alkoxy, $C_1$-$C_6$ haloalkyl, or $C_1$-$C_6$ haloalkoxy; and
R³ is $C_1$-$C_6$ alkyl, or $C_1$-$C_6$ haloalkyl.

A further embodiment provides a compound of any one of Formulae (I), (I-5), (I-6) and (I'-6), wherein $R^1$ is $C_4$ alkylene, i.e., —$(CH_2)_4$—. More specifically, the compound has one of the following structures Formula (I-7), Formula (I-8) or Formula (I'-8).

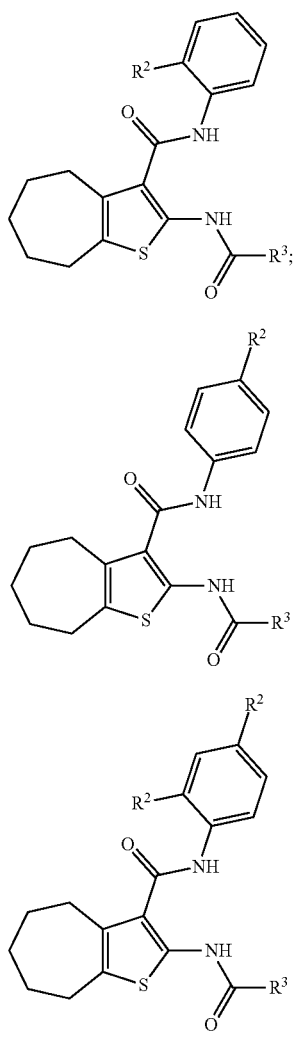

Formula (I-7)

Formula (I-8)

Formula (I'-8)

wherein:
each $R^2$ is independently hydrogen, halo, $C_1$-$C_6$ alkyl, $C_1$-$C_6$ alkoxy, $C_1$-$C_6$ haloalkyl, or $C_1$-$C_6$ haloalkoxy; and
$R^3$ is $C_1$-$C_6$ alkyl, or $C_1$-$C_6$ haloalkyl.

In more specific embodiments, the compound of any one of Formulae (I), (I-1), (I-5), (I-6), (I'-6), (I-7), (I-8) and (I'-8) is:

2-(2,2,3,3,3-pentafluoro-propionylamino)-5,6,7,8-tetrahydro4H-cyclohepta[b]thiophene-3-carboxylic acid o-tolylamide;
2-acetylamino-5,6,7,8-tetrahydro4H-cyclohepta[b]thiophene-3-carboxylic acid o-tolylamide;
2-propionylamino-5,6,7,8-tetrahydro-4H-cyclohepta[b]thiophene-3-carboxylic acid o-tolylamide;
2-(2,2,2-trifluoro-acetylamino)-5,6,7,8-tetrahydro-4H-cyclohepta[b]thiophene-3-carboxylic acid phenylamide;
2-(2,2,3,3,3-pentafluoro-propionylamino)-5,6,7,8-tetrahydro-4H-cyclohepta[b]thiophene-3-carboxylic acid phenylamide;
2-acetylamino-5,6,7,8-tetrahydro-4H-cyclohepta[b]thiophene-3-carboxylic acid phenylamide;
2-propionylamino-5,6,7,8-tetrahydro-4H-cyclohepta[b]thiophene-3-carboxylic acid phenylamide;
2-(2,2,2-trifluoro-acetylamino)-5,6,7,8-tetrahydro4H-cyclohepta[b]thiophene-3-carboxylic acid (2-ethyl-phenyl)-amide;
2-(2,2,2-trifluoro-acetylamino)-5,6,7,8-tetrahydro-4H-cyclohepta[b]thiophene-3-carboxylic acid (2-fluoro-phenyl)-amide;
2-trifluoro-acetylamino)-5,6,7,8-tetrahydro-4H-cyclohepta[b]thiophene-3-carboxylic acid (4-fluoro-phenyl)-amide;
2-(2,2,2-trifluoro-acetylamino)-5,6,7,8-tetrahydro-4H-cyclohepta[b]thiophene-3-carboxylic acid (2-chloro-phenyl)-amide;
2-(2,2,3,3,3-pentafluoro-propionylamino)-5,6,7,8-tetrahydro-4H-cyclohepta[b]thiophene-3-carboxylic acid (2-chloro-phenyl)-amide;
2-(2,2,2-trifluoro-acetylamino)-5,6,7,8-tetrahydro-4H-cyclohepta[b]thiophene-3-carboxylic acid (3-chloro-phenyl)-amide;
2-(2,2,2-trifluoro-acetylamino)-5,6,7,8-tetrahydro-4H-cyclohepta[b]thiophene-3-carboxylic acid (4-chloro-phenyl)-amide;
2-(2,2,2-trifluoro-acetylamino)-5,6,7,8-tetrahydro-4H-cyclohepta[b]thiophene-3-carboxylic acid (4-chloro-phenyl)-amide;
2-(2,2,2-trifluoro-acetylamino)-5,6,7,8-tetrahydro-4H-cyclohepta[b]thiophene-3-carboxylic acid (2-trifluoromethoxy-phenyl)-amide;
2-(2,2,3,3,3-pentafluoro-propionylamino)-5,6,7,8-tetrahydro-4H-cyclohepta[b]thiophene-3-carboxylic acid (2-trifluoromethoxy-phenyl)-amide;
2-acetylamino-5,6,7,8-tetrahydro-4H-cyclohepta[b]thiophene-3-carboxylic acid (2-trifluoromethoxy-phenyl)-amide; or
2-propionylamino-5,6,7,8-tetrahydro4H-cyclohepta[b]thiophene-3-carboxylic acid (2-trifluoromethoxy-phenyl)-amide.

Other specific embodiments provide compounds of any one of Formulae (I), (I-1), (I-5), (I-6), (I'-6), (I-7), (I-8) and (I'-8), wherein $R^3$ is $C_1$-$C_3$ perhaloalkyl. In particular, the compound is:
2-(2-chloro-2,2-difluoro-acetylamino)-5,6,7,8-tetrahydro-4H-cyclohepta[b]thiophene-3-carboxylic acid o-tolylamide;
-(2,2,3,3,4,4,4-heptafluoro-butyrylamino)-5,6,7,8-tetrahydro-4H-cyclohepta[b]thiophene-3-carboxylic acid o-tolylamide;
2(2-bromo-2,2-difluoro-acetylamino)-5,6,7,8-tetrahydro-4H-cyclohepta[b]thiophene-3-carboxylic acid o-tolylamide;
2-(2,2-Difluoro-2-iodo-acetylamino)-5,6,7,8-tetrahydro-4H-cyclohepta[b]thiophene-3-carboxylic acid o-tolylamide;
2-(2-chloro-2,2-difluoro-acetylamino)-5,6,7,8-tetrahydro4H-cyclohepta[b]thiophene-3-carboxylic acid phenylamide;
2-(2-bromo-2,2-difluoro-acetylamino)-5,6,7,8-tetrahydro-4H-cyclohepta[b]thiophene-3-carboxylic acid phenylamide;
2-(2,2-difluoro-2-iodo-acetylamino)-5,6,7,8-tetrahydro4H-cyclohepta[b]thiophene-3-carboxylic acid phenylamide;
2-(2-chloro-2,2-difluoro-acetylamino)-5,6,7,8-tetrahydro-4H-cyclohepta[b]thiophene-3-carboxylic acid (4-fluoro-phenyl)-amide;

2-(2-bromo-2,2-difluoro-acetylamino)-5,6,7,8-tetrahydro-4H-cyclohepta[b]thiophene-3-carboxylic acid (4-fluoro-phenyl)-amide;

2-(2,2-difluoro-2-iodo-acetylamino)-5,6,7,8-tetrahydro-4H-cyclohepta[b]thiophene-3-carboxylic acid (4-fluoro-phenyl)-amide; or N-(5-chloro-2-methoxyphenyl)-2-(2,2,2-trifluoroacetamido)-5,6,7,8-tetrahydro-4H-cyclohepta[b]thiophene-3-carboxamide.

Yet a further embodiment provides a compound of any one of Formulae (I), (I-5) and (I-6), wherein $R^1$ is $C_3$ alkylene, i.e., —$(CH_2)_3$—. More specifically, the compound has one of the following structures Formula (I-9) or Formula (I-10):

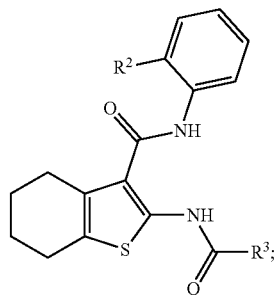

Formula (I-9)

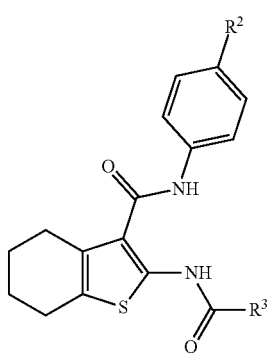

Formula (I-10)

wherein:

$R^2$ is hydrogen, halo, $C_1$-$C_6$ alkoxy, $C_1$-$C_6$ haloalkyl, or $C_1$-$C_6$ haloalkoxy; and $R^3$ is $C_1$-$C_6$ alkyl, or $C_1$-$C_6$ haloalkyl.

In more specific embodiments, the compound of any of one of Formulae (I), (I-2), (I-5), (I-6), (I-9) and (I-10) is:

2-(2,2,2-trifluoro-acetylamino)-4,5,6,7-tetrahydro-benzo[b]thiophene-3-carboxylic acid phenylamide;

2-(2,2,2-trifluoro-acetylamino)-4,5,6,7-tetrahydro-benzo[b]thiophene-3-carboxylic acid o-tolylamide;

2-(2,2,2-trifluoro-acetylamino)-4,5,6,7-tetrahydro-benzo[b]thiophene-3-carboxylic acid p-tolylamide; or 2-(2,2,2-trifluoro-acetylamino)-4,5,6,7-tetrahydro-benzo[b]thiophene-3-carboxylic acid (4-fluoro-phenyl)-amide.

A further embodiment provides a compound of any one of Formulae (I), (I-5) or (I-6), wherein $R^1$ is $C_2$ alkylene, i.e., —$(CH_2)_2$—. More specifically, the compound has one of the following structures Formula (I-11) or Formula (I-12):

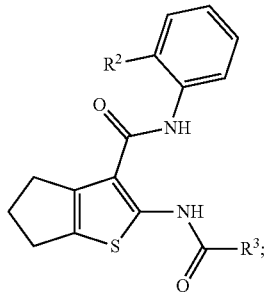

Formula (I-11)

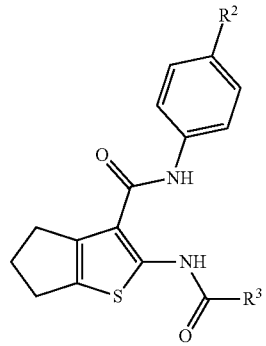

Formula (I-12)

wherein:

$R^2$ is hydrogen, halo, $C_1$-$C_6$ alkyl, $C_1$-$C_6$ alkoxy, $C_1$-$C_6$ haloalkyl, or $C_1$-$C_6$ haloalkoxy; and $R^3$ is $C_1$-$C_6$ alkyl, or $C_1$-$C_6$ haloalkyl.

In more specific embodiments, the compound of any of one of Formulae (I), (I-3), (I-5), (I-6), (I-11) and (I-12) is:

2-(2,2,2-trifluoro-acetylamino)-5,6-dihydro-4H-cyclopenta[b]thiophene-3-carboxylic acid o-tolylamide;

2-(2,2,3,3,3-pentafluoro-propionylamino)-5,6-dihydro-4H-cyclopenta[b]thiophene-3-carboxylic acid o-tolylamide;

2-acetylamino-5,6-dihydro-4H-cyclopenta[b]thiophene-3-carboxylic acid o-tolylamide;

2-propionylamino-5,6-dihydro-4H-cyclopenta[b]thiophene-3-carboxylic acid o-tolylamide;

2-(2,2,2-trifluoro-acetylamino)-5,6-dihydro-4H-cyclopenta[b]thiophene-3-carboxylic acid p-tolylamide;

2-(2,2,2-trifluoro-acetylamino)-5,6-dihydro-4H-cyclopenta[b]thiophene-3-carboxylic acid (2-chloro-phenyl)-amide;

2-(2,2,2-trifluoro-acetylamino)-5,6-dihydro-4H-cyclopenta[b]thiophene-3-carboxylic acid (2-trifluoromethoxy-phenyl)-amide;

2-(2-chloro-2,2-difluoro-acetylamino)-5,6-dihydro-4H-cyclopenta[b]thiophene-3-carboxylic acid (2-trifluoromethoxy-phenyl)-amide;

2-(2-bromo-2,2-difluoro-acetylamino)-5,6-dihydro-4H-cyclopenta[b]thiophene-3-carboxylic acid (4-methyl-2-trifluoromethoxy-phenyl)-amide; or 2-(2,2-difluoro-2-iodo-acetylamino)-5,6-dihydro-4H-cyclopenta[b]thiophene-3-carboxylic acid (2-trifluoromethoxy-phenyl)-amide.

In still other embodiments, it is provided a compound of any one of Formulae (I), (I-5) and (I-6) wherein $R^1$ is $C_2$ heteroalkylene, including for example —$(CH_2$—O—$CH_2)$— and $(CH_2$—$CH_2$—O)—. In particular, one embodiment provides a compound having one of the following structures Formula (I-13) or Formula (I-14):

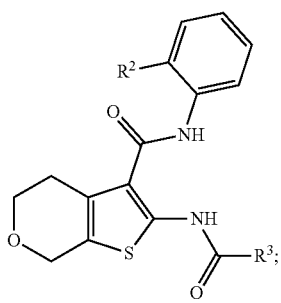

Formula (I-13)

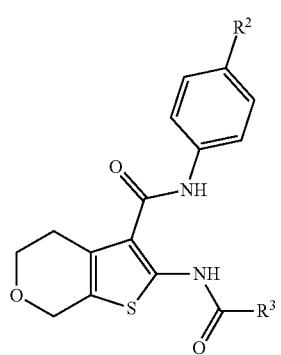

Formula (I-14)

wherein:

$R^2$ is hydrogen, halo, $C_1$-$C_6$ alkyl, $C_1$-$C_6$ alkoxy, $C_1$-$C_6$ haloalkyl, or $C_1$-$C_6$ haloalkoxy; and $R^3$ is $C_1$-$C_6$ alkyl, or $C_1$-$C_6$ haloalkyl.

In more specific embodiments, the compound of any of one of Formulae (I), (I-4), (I-5), (I-6), (I-13) and (I-14) is:
2-(2,2,3,3,3-pentafluoro-propionylamino)-4,7-dihydro-5H-thieno[2,3-c]pyran-3-carboxylic acid o-tolylamide;
2-propionylamino-4,7-dihydro-5H-thieno[2,3-c]pyran-3-carboxylic acid o-olylamide;
2-(2,2,2-trifluoro-acetylamine)-4,7-dihydro-5H-thieno[2,3-c]pyran-3-carboxylic acid (2-chloro-phenyl)-amide;
2-(2,2,2-trifluoro-acetylamino)-4,7-dihydro-5H-thieno[2,3-c]pyran-3-carboxylic acid p-tolylamide; or
2-(2,2,2-trifluoro-acetylamino)-4,7-dihydro-5H-thieno[2,3-c]pyran-3-carboxylic acid (4-fluoro-phenyl)-amide.

In various specific embodiments, $R^1$ is butylene, propylene, ethylene, or —$CH_2OCH_2$—. In some specific embodiments, $R^1$ is butylene. In some embodiments, $R^1$ is propylene. In some embodiments, $R^1$ is ethylene. In some embodiments, $R^1$ is —$CH_2OCH_2$—.

In various specific embodiments, $R^2$ is hydrogen, methyl, ethyl, trifluoromethyl, trifluoromethoxy, fluoro, or chloro. In some embodiments, $R^2$ is H. In some embodiments, $R^2$ is methyl. In some embodiments, $R^2$ is ethyl. In some embodiments, $R^2$ is trifluoromethyl. In some embodiments, $R^2$ is trifluoromethoxy. In some embodiments, $R^2$ is fluoro. In some embodiments, $R^2$ is chloro.

In some of the foregoing embodiments, $R^3$ is methyl, ethyl, trifluoromethyl, pentafluoroethyl, heptafluoropropyl, chlorodifluoromethyl, bromodifluoromethyl, or difluoroiodomethyl. In some embodiments, $R^3$ is methyl. In some embodiments, $R^3$ is ethyl. In some embodiments, $R^3$ is trifluoromethyl. In some embodiments, $R^3$ is pentafluoroethyl. In some embodiments, $R^3$ is heptafluoroethyl. In some embodiments, $R^3$ is chlorodifluoromethyl. In some embodiments, $R^3$ is bromodifluoromethyl. In some embodiments, $R^3$ is difluoroiodomethyl.

Chemistry Definitions

"Alkyl" means a straight chain or branched, noncyclic, unsaturated or partially unsaturated aliphatic hydrocarbon containing from 1 to 12 carbon atoms. A lower alkyl refers to an alkyl that has any number of carbon atoms between 1 and 6 (i.e., $C_1$-$C_6$ alkyl). Representative saturated straight chain alkyls include methyl, ethyl, n-propyl, n-butyl, n-pentyl, n-hexyl, and the like, while saturated branched alkyls include isopropyl, sec-butyl, isobutyl, tert-butyl, tert-pentyl, heptyl, n-octyl, isopentyl, 2-ethylhexyl and the like. Alkyl may be optionally substituted by one or more substituents as defined herein.

"Alkoxy" refers to the radical of —O-alkyl. Examples of alkoxy include methoxy, ethoxy, and the like. The alkyl moiety of alkoxy may be optionally substituted by one or more substituents as defined herein.

"Alkylene" refers to a straight or branched divalent hydrocarbon chain linking the rest of the molecule (e.g., forming a cycloalkyl ring), consisting solely of carbon and hydrogen, having from one to twelve carbon atoms, or more typically one to six carbons. Examples include methylene ($C_1$ alkylene), ethylene ($C_2$ alkylene), propylene ($C_3$ alkylene), or butylene ($C_4$ alkylene), and the like. The alkylene chain is attached to the rest of the molecule through respective single C—C bond. Alkylene may be optionally substituted by one or more substituents as defined herein.

"Aryl" means an aromatic carbocyclic moiety such as phenyl or naphthyl (i.e., naphthalenyl) (1- or 2-naphthyl) or anthracenyl (e.g., 2-anthracenyl).

"Arylalkyl" (e.g., phenylalkyl) means an alkyl having at least one alkyl hydrogen atom replaced with an aryl moiety, such as —$CH_2$-phenyl, —CH=CH-phenyl, —$C(CH_3)$=CH-phenyl, and the like.

"Heteroalkylene" refers to a straight or branched divalent hydrocarbon chain linking the rest of the molecule, wherein one or more of the carbon atoms in the divalent chain are replaced by one or more heteroatoms, including oxygen, nitrogen or sulfur. A heteroalkylene radical may comprise from one to eleven carbon atoms, or more typically one to five carbon atoms. Typically, heteroalkylene comprises one oxygen atom (—O—), one nitrogen (—NH—) or one sulfur (—O—) in the chain. The alkylene chain is attached to the rest of the molecule through respective single C—C bond or C—O bond, or C—NH bond, or C—S bond. Heteroalkylene may be optionally substituted by one or more substituents as defined herein.

"Halogen" or "halo" means fluoro, chloro, bromo, and iodo.

"Haloalkyl" refers to a halo-substituted alkyl, i.e., alkyl in which at least one hydrogen atom is replaced with halogen. "Perhaloalkyl" refers to haloalkyl in which all of the hydrogens are replaced by halogens. Examples of haloalkyls include trifluoromethyl, chlorodifluoromethyl, bromodifluoromethyl, 1,1,2,2,3,3,3-heptafluoropropyl and the like. In certain embodiments, the halo substituents of a haloalkyl or perhaloalkyl may be the same (e.g., all of the halo substituents are fluoro) or different (e.g., the halo substituents may be a mixture of any two or more of fluoro, chloro, bromo or iodo). The alkyl moiety of a haloalkyl may be optionally substituted by one or more substituents as defined herein.

"Haloalkoxy" refers to a substituted alkoxy, means an alkoxy moiety having at least one hydrogen atom replaced with halogen, such as chloromethoxy and the like.

All the above groups may be "optionally substituted," i.e., either substituted or unsubstituted. The term "substituted" as used herein means any of the above groups (i.e., alkyl, alkylene, alkoxy, alkoxyalkyl, aryl, aralkyl, heterocyclyl, heterocyclylalkyl, heteroaryl, heteroarylalkyl and/or trifluoroalkyl), may be further functionalized wherein at least one hydrogen atom is replaced by a bond to a non-hydrogen atom substituent. Unless stated specifically in the specification, a substituted group may include one or more substituents selected from: oxo, nitrile, nitro, —CONH$_2$, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkyl carbonyl, cycloalkylalkylcarbonyl, cycloalkyloxycarbonyl, heterocyclyl, heteroaryl, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, thioalkyl triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, —NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —CH$_2$SO$_2$R$_g$, —CH$_2$SO$_2$NR$_g$R$_h$, —SH, —SR$_g$ or —SSR$_g$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents.

Synthetic Schemes

The AACT derivatives of any one of Formulae (I) and (I-1)-(I-14) may be prepared using the modular synthetic strategy shown in Scheme 1.

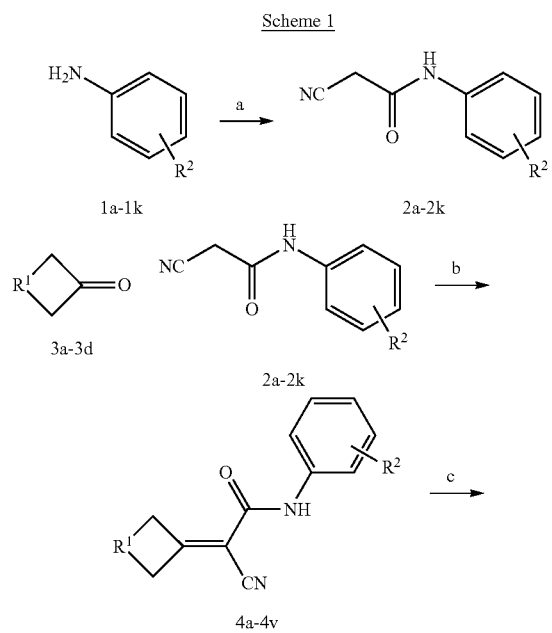

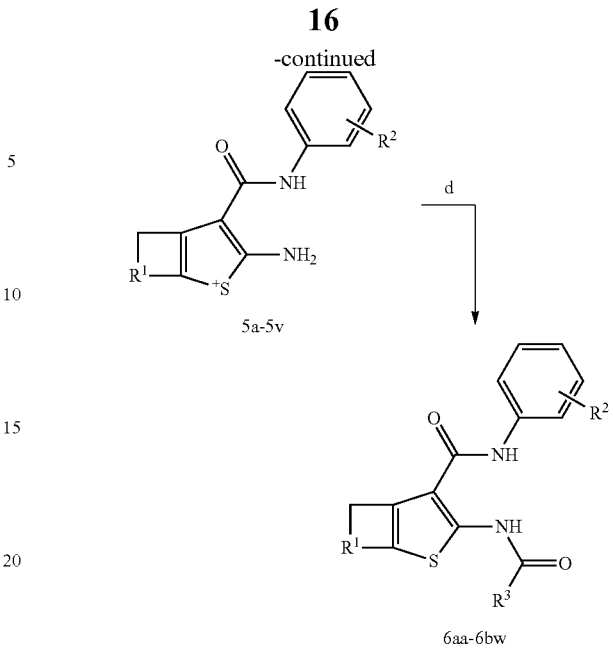

Reagents and conditions: (a) cyanoacetic acid (1.0 eq) and EDCI-HCl (1.2 eq) (rt, 6 min); (b) cycloalkyl ketone, NH4OAc, and AcOH (100° C., 60 min); (c) S8, morpholine (3.0 eq), EtOH (90° C., 5h); (d) electrophilic acylating agent (1.3 eq), Et3N (1.3 eq) (rt, 10 min) or difluoroiodoacetic acid (1.2 eq) and EDCI-HCl (1.5 eq) (rt, 60 min).

The synthesis begins with the generation of substituted aryl cyanoacetamides, followed by a two-step Knoevenagel-Gewald sequence to generate 2-aminothiophenes, and coupling with simple electrophilic acylating agents. Substituted anilines (1a-1k) were coupled with cyanoacetic acid using EDCI-HCl to generate the library of cyanoacetamides (2a-2k). The substituent composition of this library, prepared typically in good yields, are also shown in Table 1, with some of the cyanoacetamides also being commercially available.

TABLE 1

| Product Cyanoacetamide | SM Aniline | R$^2$ | Isolated Yield (%) |
|---|---|---|---|
| 2a | 1a | 2-(CH$_3$) | 50 |
| 2b | 1b | H | purchased |
| 2c | 1c | 2-(CH$_2$CH$_3$) | 76 |
| 2d | 1d | 2-F | 78 |
| 2e | 1e | 4-F | 70 |
| 2f | 1f | 2-Cl | 82 |
| 2g | 1g | 3-Cl | 80 |
| 2h | 1h | 4-Cl | 89 |
| 2i | 1i | 4-(CF$_3$) | 79 |
| 2j | 1j | 4-(CH$_3$) | 86 |
| 2k | 1k | 2-(OCF$_3$) | 87 |

Next, the substituted aryl cyanoacetamides (2a-2k) were condensed with a small collection of cycloalkyl ketones (3a-3c) under buffered acid-catalyzed aldol conditions (AcOH:NH$_4$OAc) to generate Knoevenagel adducts (4a-4v). While excess cyclic ketone was useful to obtain high conversion, we were pleased that this material could be removed by evaporation. The Knoevenagel adducts were subjected to the Gewald cyclization reaction in the presence of molecular octasulfur (S$_g$), to yield 2-amino-cycloalkylthiophene-3-carboxylic acid arylamides (5a-5v), which were typically crystalline and easily purified by trituration. The composition of the library and yields for the Knoevenagel and Gewald reactions are shown in Table 2, separated by the different cycloalkyl ketones.

TABLE 2

| Product Amino-thiophene | SM Cyano-acetamide | Isolated Yield (%) Intmdt 4 | Isolated Yield (%) Intmdt 5 | $R^1$ | $R^2$ |
|---|---|---|---|---|---|
| (based on cycloheptanone 3a) | | | | | |
| 5a | 2a | 87 | 50 | —(CH$_2$)$_4$— | 2-(CH$_3$) |
| 5b | 2b | 52 | 90 | —(CH$_2$)$_4$— | H |
| 5c | 2c | 48 | 70 | —(CH$_2$)$_4$— | 2-(CH$_2$CH$_3$) |
| 5d | 2d | 93 | 51 | —(CH$_2$)$_4$— | 2-F |
| 5e | 2e | 60 | 69 | —(CH$_2$)$_4$— | 4-F |
| 5f | 2f | 70 | 85 | —(CH$_2$)$_4$— | 2-Cl |
| 5g | 2g | 73 | 93 | —(CH$_2$)$_4$— | 3-Cl |
| 5h | 2h | 90 | 67 | —(CH$_2$)$_4$— | 4-Cl |
| 5i | 2i | 76 | 98 | —(CH$_2$)$_4$— | 4-(CF$_3$) |
| 5j | 2j | 58 | 7 | —(CH$_2$)$_4$— | 2-(OCF$_3$) |
| (based on cyclohexanone 3b) | | | | | |
| 5k | 2b | 70 | 62 | —(CH$_2$)$_3$— | H |
| 5l | 2a | 90 | 95 | —(CH$_2$)$_3$— | 2-(CH$_3$) |
| 5m | 2j | 55 | 37 | —(CH$_2$)$_3$— | 4-(CH$_3$) |
| 5n | 2e | 32 | 97 | —(CH$_2$)$_3$— | 4-F |
| (based on tetrahydro-4H-pyran-4-one 3c) | | | | | |
| 5o | 2a | 86 | 92 | —CH$_2$OCH$_2$— | 2-(CH$_3$) |
| 5p | 2f | 66 | 21 | —CH$_2$OCH$_2$— | 2-Cl |
| 5q | 2j | 55 | 23 | —CH$_2$OCH$_2$— | 4-(CH$_3$) |
| 5r | 2e | 70 | 26 | —CH$_2$OCH$_2$— | 4-F |
| (based on cyclopentanone 3d) | | | | | |
| 5s | 2a | 60 | 92 | —(CH$_2$)$_2$— | 2-(CH$_3$) |
| 5t | 2j | 60 | 55 | —(CH$_2$)$_2$— | 4-(CH$_3$) |
| 5u | 2f | 84 | 72 | —(CH$_2$)$_2$— | 2-Cl |
| 5v | 2k | 38 | 82 | —(CH$_2$)$_2$— | 2-(OCF$_3$) |

Finally, coupling of the aminothiophenes (5a-5v) with alkyl and fluoroalkyl acyl chlorides, anhydrides, or EDCI-coupling was done to generate the final desired AACT compounds (6aa-6bw), also typically as crystalline solids, in fair to good yields (Table 3). After completion of a 1$^{st}$ generation of compounds (6aa-6bj) based on simple alkyl and fluoroalkyl groups at the $R^3$ position, we designed a 2$^{nd}$ generation library with halodifluoroalkyl (chloro, bromo, and iodo) and heptafluorobutyryl at $R^3$, based on the most promising combinations of $R^1$ and $R^2$ (6bk-6bw). The synthesis of the difluoroiodoacetyl inhibitors (6bn, 6bq, 6bt, and 6bw) was accomplished by EDCI-mediated coupling of aminothiophenes with difluoroiodoacetic acid. In total, 49 inhibitor candidates were prepared by variations at the $R^1$, $R^2$, and $R^3$ positions. The structure and purity of the final products were confirmed by $^1$H-NMR, ESI-LCMS (UV absorption detection at 254 nm), with purities estimated to be >95%.

TABLE 3

| Product Final | SM amino thiophene | $R^1$ | $R^2$ | $R^3$ | Isolated yield (%) | FPR IC$_{50}$ TMEM16A (μM) |
|---|---|---|---|---|---|---|
| (based on cycloheptanone 3a) | | | | | | |
| 6aa | 5a | —(CH$_2$)$_4$— | 2-(CH$_3$) | CF$_3$ | 61 | 0.42 |
| 6ab | 5a | —(CH$_2$)$_4$— | 2-(CH$_3$) | CF$_2$CF$_3$ | 65 | 1.3 |
| 6ac | 5a | —(CH$_2$)$_4$— | 2-(CH$_3$) | CH$_3$ | 82 | >10 |
| 6ad | 5a | —(CH$_2$)$_4$— | 2-(CH$_3$) | CH$_2$CH$_3$ | 70 | >20 |
| 6ae | 5b | —(CH$_2$)$_4$— | H | CF$_3$ | 38 | 0.3 |
| 6af | 5b | —(CH$_2$)$_4$— | H | CF$_2$CF$_3$ | 97 | 2.5 |
| 6ag | 5b | —(CH$_2$)$_4$— | H | CH$_3$ | 80 | >20 |
| 6ah | 5b | —(CH$_2$)$_4$— | H | CH$_2$CH$_3$ | 87 | 1.2 |
| 6ai | 5c | —(CH$_2$)$_4$— | 2-(CH$_2$CH$_3$) | CF$_3$ | 6 | 1.3 |
| 6aj | 5d | —(CH$_2$)$_4$— | 2-F | CF$_3$ | 48 | 1.3 |
| 6ak | 5e | —(CH$_2$)$_4$— | 4-F | CF$_3$ | 60 | 0.32 |
| 6al | 5f | —(CH$_2$)$_4$— | 2-Cl | CF$_3$ | 87 | 0.66 |
| 6am | 5f | —(CH$_2$)$_4$— | 2-Cl | CF$_2$CF$_3$ | 91 | >20 |
| 6an | 5g | —(CH$_2$)$_4$— | 3-Cl | CF$_3$ | 23 | 5 |
| 6ao | 5h | —(CH$_2$)$_4$— | 4-Cl | CF$_3$ | 4 | 3 |
| bap | 5i | —(CH$_2$)$_4$— | 4-(CF$_3$) | CF$_3$ | 2 | 5 |
| 6aq | 5j | —(CH$_2$)$_4$— | 2-(OCF$_3$) | CF$_3$ | 12 | 1.3 |
| 6ar | 5j | —(CH$_2$)$_4$— | 2-(OCF$_3$) | CF$_2$CF$_3$ | 30 | 2.7 |
| 6as | 5j | —(CH$_2$)$_4$— | 2-(OCF$_3$) | CH$_3$ | 55 | >20 |
| 6at | 5j | —(CH$_2$)$_4$— | 2-(OCF$_3$) | CH$_2$CH$_3$ | 50 | >20 |
| (based on cyclohexanone 3b) | | | | | | |
| 6au | 5k | —(CH$_2$)$_3$— | H | CF$_3$ | 93 | 0.37 |
| 6av | 5l | —(CH$_2$)$_3$— | 2-(CH$_3$) | CF$_3$ | 17 | 0.17 |
| 6aw | 5m | —(CH$_2$)$_3$— | 4-(CH$_3$) | CF$_3$ | 30 | 0.22 |
| 6ax | 5n | —(CH$_2$)$_3$— | 4-F | CF$_3$ | 48 | 0.49 |
| (based on tetrahydro-4H-pyran-4-one 3c) | | | | | | |
| 6ay | 5o | —CH$_2$OCH$_2$— | 2-(CH$_3$) | CF$_2$CF$_3$ | 6 | 1.6 |
| 6az | 5o | —CH$_2$OCH$_2$— | 2-(CH$_3$) | CH$_2$CH$_3$ | 40 | 3 |
| 6ba | 5p | —CH$_2$OCH$_2$— | 2-Cl | CF$_3$ | 67 | 1.3 |
| 6bb | 5q | —CH$_2$OCH$_2$— | 4-(CH$_3$) | CF$_3$ | 38 | 5 |
| 6bc | 5r | —CH$_2$OCH$_2$— | 4-F | CF$_3$ | 15 | 3.8 |

TABLE 3-continued

| Product Final | SM amino thiophene | R¹ | R² | R³ | Isolated yield (%) | FPR IC$_{50}$ TMEM16A (μM) |
|---|---|---|---|---|---|---|
| (based on cyclopentanone 3d) | | | | | | |
| 6bd | 5s | —(CH$_2$)$_2$— | 2-(CH$_3$) | CF$_3$ | 10 | >20 |
| 6be | 5s | —(CH$_2$)$_2$— | 2-(CH$_3$) | CF$_2$CF$_3$ | 37 | 6.2 |
| 6bf | 5s | —(CH$_2$)$_2$— | 2-(CH$_3$) | CH$_3$ | 38 | >20 |
| 6bg | 5s | —(CH$_2$)$_2$— | 2-(CH$_3$) | CH$_2$CH$_3$ | 33 | >20 |
| 6bh | 5t | —(CH$_2$)$_2$— | 4-(CH$_3$) | CF$_3$ | 77 | 2.5 |
| 6bi | 5u | —(CH$_2$)$_2$— | 2-Cl | CF$_3$ | 64 | 1.3 |
| 6bj | 5v | —(CH$_2$)$_2$— | 2-(OCF$_3$) | CF$_3$ | 56 | 0.37 |
| (2$^{nd}$-generation inhibitors with perhaloalkyl R³ substituents) | | | | | | |
| 6bk | 5a | —(CH$_2$)$_4$— | 2-(CH$_3$) | CF$_2$Cl | 27 | 0.18 |
| 6bl | 5a | —(CH$_2$)$_4$— | 2-(CH$_3$) | CF$_2$CF$_2$CF$_3$ | 61 | 0.38 |
| 6bm | 5a | —(CH$_2$)$_4$— | 2-(CH$_3$) | CF$_2$Br | 36 | 0.083 |
| 6bn | 5a | —(CH$_2$)$_4$— | 2-(CH$_3$) | CF$_2$I | 67 | 0.6 |
| 6bo | 5b | —(CH$_2$)$_4$— | H | CF$_2$Cl | 16 | 0.925 |
| 6bp | 5b | —(CH$_2$)$_4$— | H | CF$_2$Br | 15 | 0.23 |
| 6bq | 5b | —(CH$_2$)$_4$— | H | CF$_2$I | 13 | 0.23 |
| 6br | 5e | —(CH$_2$)$_4$— | 4-F | CF$_2$Cl | 19 | 0.84 |
| 6bs | 5e | —(CH$_2$)$_4$— | 4-F | CF$_2$Br | 32 | 0.45 |
| 6bt | 5e | —(CH$_2$)$_4$— | 4-F | CF$_2$I | 60 | 0.15 |
| 6bu | 5v | —(CH$_2$)$_2$— | 2-(OCF$_3$) | CF$_2$Cl | 81 | >20$^a$ |
| 6bv | 5v | —(CH$_2$)$_2$— | 2-(OCF$_3$) | CF$_2$Br | 40 | 0.70$^a$ |
| 6bw | 5v | —(CH$_2$)$_2$— | 2-(OCF$_3$) | CF$_2$I | 50 | 1.88 |

$^a$Low solubility in DMSO

Biological Characterization

2-Acylamino-cycloalkylthiophene-3-carboxylic acid arylamides 6aa-6bw were initially evaluated for inhibition of TMEM16A anion channel function using a cell-based functional plate reader assay as reported. (See Namkung, W. et al., Faseb J 2011, 25, (11), 4048-4062; Namkung, W. et al., J Biol Chem 2011, 286, (3), 2365-74; Piechowicz, K. A. et al., J Enzyme Inhib Med Chem 2016, 1-7.) IC$_{50}$ values determined from concentration-inhibition measurements are summarized in Table 3.

The 1$^{st}$ generation library (6aa-6bj) showed several compounds with apparent IC$_{50}$ of 0.2-0.3 μM. 6baa (initial inhibitor), 6ae, 6ak, 6au, 6av, 6aw. These results showed that 5-, 6-, and 7-member rings were tolerated at the R¹ position, while compounds based on tetrahydro-4H-pyran-4-one (6ay-6bc) were inactive. The best inhibitors contained H, 2- or 4-(CH$_3$), or 4-F on the aromatic ring (R²), and CF$_3$ as the acylamido substituent (R³). Inhibitors with differing groups at R², such as 2-F, 2-Cl, 3-Cl, 4-Cl, 4-(CF$_3$), 2-(OCF$_3$), were less potent. Likewise, compounds with alternative substituents at R³, including CF$_2$CF$_3$, CH$_3$, and CH$_2$CH$_3$, also had reduced potency.

Based on results that favored CF$_3$ at the R³ position, we designed a 2$^{nd}$-generation library (6bk-6bw) that incorporated novel groups such as chlorodifluoro, bromodifluoro, or difluoroiodo, probing steric and electronic effects at that position. Additionally, we prepared one compound that incorporated a heptafluorobutyryl substituent (6bl) to evaluate the effect of a multi-carbon fluoroalkyl group. Gratifyingly, we found three 2$^{nd}$-generation compounds with lower apparent IC$_{50}$ of 0.08-0.18 μM: 6bk, 6bm, and 6bt.

Figure 2:
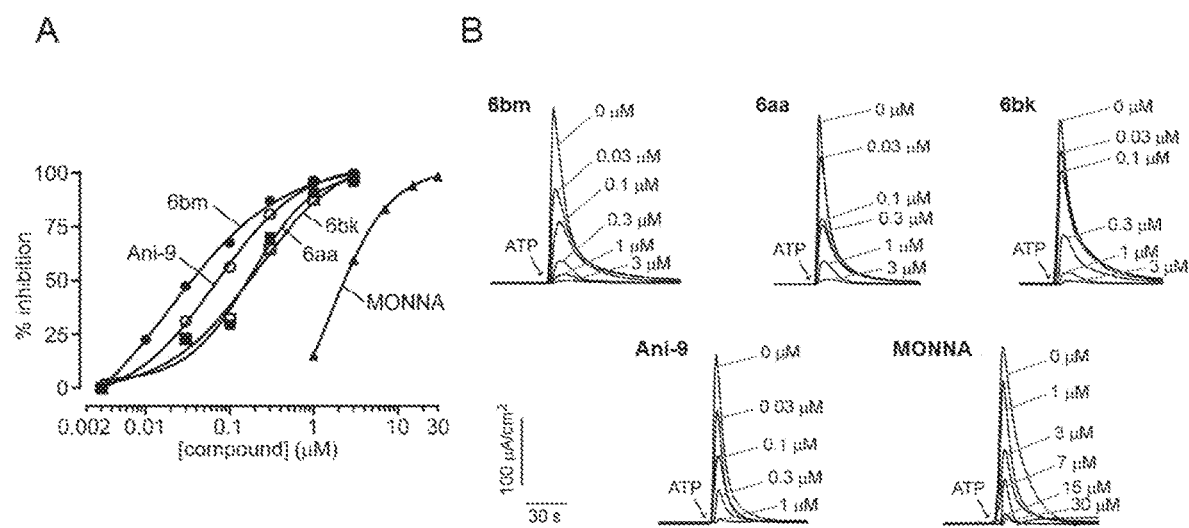
FIG. 2 shows short-circuit current measurement of TMEM16A inhibition by Compounds 6aa, 6bk, and 6bm, and previously reported compounds Ani-9 and MONNA. Measurements were done in FRT cells expressing TMEM16A. (A) Summary of dose-response data (mean±S.E., n=3). (B) Examples of original data in which inhibitors were added 5 min prior to TMEM16A activation by 100 μM ATP.

The most potent TMEM16A inhibitors identified using the semi-quantative plate reader assay were then studied using a definitive short-circuit current assay in which measured current is a direct, quantitative measure of TMEM16A Cl⁻ conductance. Compounds 6aa (original inhibitor from screen), 6ae, 6bk, 6bm, 6bn and 6bt were tested, and compared with previously reported inhibitors MONNA, Ani-9 and T16A$_{inh}$-A01. Concentration-dependence for selected compounds is shown in FIG. 2, with IC$_{50}$ values summarized in Table 4. By short-circuit current assay, 6aa showed an IC$_{50}$ of 0.26 μM, similar to the chlorodifluoroacetamide 6bk with IC$_{50}$ of 0.23 μM. Difluoroiodoacetamides 6bn and 6bt were less potent with IC$_{50}$ of 0.73 and 0.60 μM, respectively. Notably, bromodifluoroacetamide 6bm had IC$_{50}$ of 0.030 μM.

Table 4 shows certain characterizations of AACT derivatives disclosed herein. Concentration-dependent inhibition of TMEM16A measured by short-circuit current assay; TMEM16B and non-TMEM16 anion conductance measured using a fluorescence plate reader assay using FRT and HT-29 cells respectively; cell viability measured in FRT null cells.

TABLE 4

| Inhibitor | R¹ | R² | R³ | TMEM16A IC$_{50}$ (μM) | TMEM16B IC$_{50}$ (μM) | HT-29 IC$_{50}$ (μM) | Cellular survival % at 5 μM |
|---|---|---|---|---|---|---|---|
| 6aa | —(CH$_2$)$_4$— | 2-(CH$_3$) | CF$_3$ | 0.26 | 1.4 | 4.0 | 99 |
| 6ae | —(CH$_2$)$_4$— | H | CF$_3$ | 0.13 | 4.6 | 5.0 | 97 |
| 6bk | —(CH$_2$)$_4$— | 2-(CH$_3$) | CF$_2$Cl | 0.23 | 0.4 | 9.5 | 98 |
| 6bm | —(CH$_2$)$_4$— | 2-(CH$_3$) | CF$_2$Br | 0.030 | 0.4 | 5.4 | 97 |
| 6bn | —(CH$_2$)$_4$— | 2-(CH$_3$) | CF$_2$I | 0.73 | 1.4 | 3.5 | 96 |
| 6bt | —(CH$_2$)$_4$— | 4-F | CF$_2$I | 0.60 | 1.1 | 5.0 | 97 |

Ion channel specificity and cytotoxicity were determined for the six most potent AACT compounds (Table 4). Selectivity was studied for TMEM16B, an isoform of TMEM16A that also functions as a $Ca^{2+}$-activated $Cl^-$ channel. The AACT inhibitors were relatively non-selective against TMEM16B, with $IC_{50}$ from 0.4-1.4 μM. Two of the more potent TMEM16A inhibitors (6bk and 6bm) were also among the more potent against TMEM16B with $IC_{50}$ ~0.4 μM. We further assayed the compound potency on endogenous non-TMEM16A. $Ca^{2+}$-activated $Cl^-$ channel in HT-29 cells. (See De La Fuente, R. et al., *Mol Pharmacol* 2008, 73, (3), 758-68.) In general, the AACT compounds were weak inhibitors of CaCCs in HT-29 cells ($IC_{50}$ 3.5-9.5 μM). None of the compounds examined showed significant toxicity using an Alamar blue assay at concentrations up to 5 μM. Additionally, none of the compounds inhibited the cAMP-activated $Cl^-$ channel cystic fibrosis transmembrane conductance regulator (CFTR) (data not shown).

Figure 3:
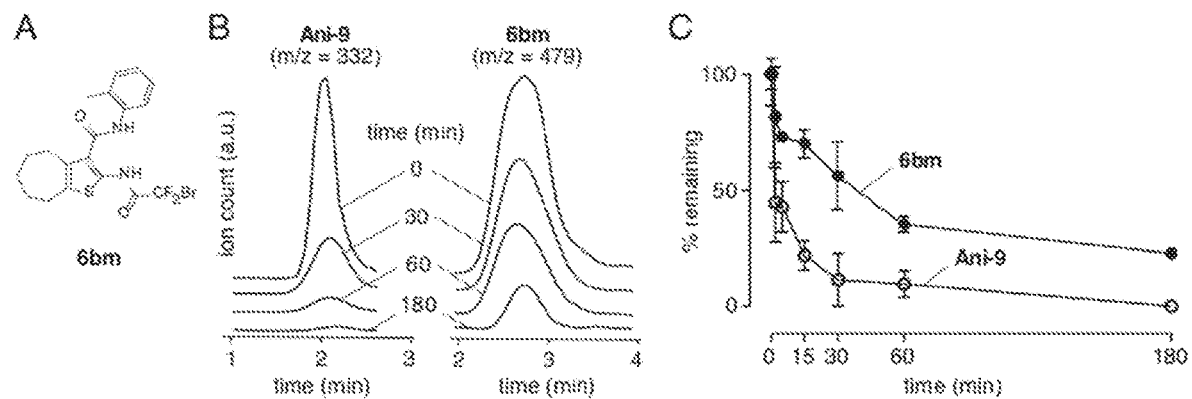
FIG. 3A-3C show microsomal stability of Compounds 6bm and Ani-9 in the presence of hepatic microsomes and NADPH. (3A) Structure of Compound 6bm. (3B) LC/MS traces showing total ion counts as a function of incubation time. (3C) Summary of in vitro metabolic stability shows percent of remaining compounds over time (mean±S.E.M., n=3).

In vitro metabolic stability was determined using a hepatic microsome assay for the most potent inhibitor 6bm (FIG. 3(A)) and previously reported Ani-9. These compounds were incubated with rat liver microsomes and NADPH, and non-metabolized compounds were quantified by ESI-LCMS. FIG. 3(B) shows near complete degradation of Ani-9 at 180 min, whereas for the same incubation time ~30% of 6bm remained. FIG. 3C summarizes the time course of compound degradation showing remarkably greater stability of 6bm compared to Ani-9. 6bm could be potentially metabolized by amide-bond hydrolysis or oxidation of the benzene or aryl methyl. It is speculated that Ani-9 could be oxidized at the aryl methyl or N—N bond; or hydrolyzed at the amide or hydrazone linkages.

Figure 4:
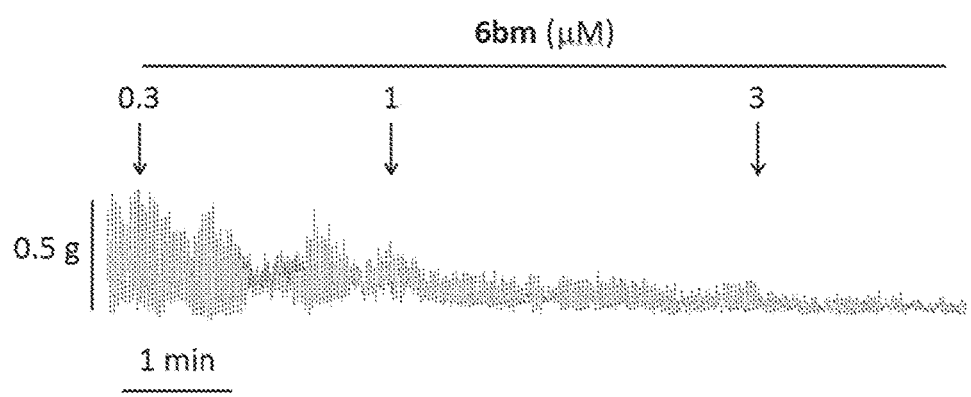
FIG. 4 shows the inhibition of isometric smooth muscle contractions of ex vivo mouse ileum by Compound 6bm. Response to increasing concentrations of 6bm showed suppression of isometric smooth muscle contractions (data is representative of three separate experiments).

To demonstrate one predicted biological action of TMEM16A inhibition, we measured intestinal smooth muscle contraction. The effect of 6bm was determined when added to the bath in an ex vivo preparation of mouse ileum. As is shown in FIG. 4, 6bm strongly inhibited spontaneous isometric contractions of ileum in a concentration-dependent manner.

Pharmaceutical Composition

Also provided herein is a pharmaceutical composition comprising a physiologically acceptable excipient and a compound of Formula (I):

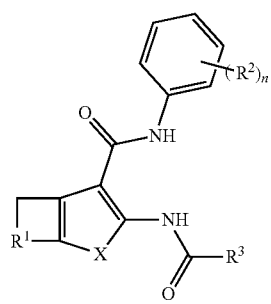

Formula (I)

or a pharmaceutically acceptable salt, isotopic form, stereoisomer or prodrug thereof, wherein:
n is 1, 2, 3 or 4;
X is S, O, or NR;
R is hydrogen or $C_1$-$C_6$ alkyl;
$R^1$ is optionally substituted $C_1$-$C_6$ alkylene or optionally substituted $C_1$-$C_5$ heteroalkylene;

each $R^2$ is the same or different and independently hydrogen, halo, $C_1$-$C_6$ alkyl, $C_1$-$C_6$ alkoxy, $C_1$-$C_6$ haloalkyl, or $C_1$-$C_6$ haloalkoxy; and
$R^3$ is $C_1$-$C_6$ alkyl, or $C_1$-$C_6$ haloalkyl.

In various embodiments, the pharmaceutical composition comprising a compound of Formula (I) may have substructures as represented by any one of Formulae (I-1), (I'-1), (I-2), (I-3), (I-4), (I-5), (I-6), (I'-6), (I-7), (I-8), (I'-8), (I-9), (I-10), (I-11), (I-12), (I-13) or (I-14), or any one of Formulae (I-1a), (I'-1a), (I-2a), (I-3a), or (I-4a).

A pharmaceutical composition may be a sterile aqueous or non-aqueous solution, suspension or emulsion, which additionally comprises a physiologically acceptable excipient (also called a pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Use and Method of Treatment

Also provided herein is a method of inhibiting a calcium-activated chloride channel comprising: contacting (a) a cell that comprises the calcium-activated chloride channel and (b) a pharmaceutical composition comprising a compound of Formula (I) or any one of the substructures as represented by Formulae (I-1)-(I-14), in an amount effective and under conditions and for a time sufficient to inhibit activation of the channel. In a specific embodiment, the cell is an epithelial cell. In a particular embodiment, the epithelial cell is an intestinal epithelial cell or a lung epithelial cell. In a specific embodiment, the calcium-activated chloride channel is TMEM16A, and in other specific embodiments, the TMEM16A calcium-activated chloride channel is a human TMEM16A calcium-activated chloride channel. In a specific embodiment, the compound is 2-(2-bromo-2,2-difluoroacetylamino)-5,6,7,8-tetrahydro-4H-cyclohepta[b]thiophene-3-carboxylic acid o-tolylamide.

In one embodiment, provided herein is a method of inhibiting fluid secretion from a cell comprising administering to a subject of a pharmaceutical composition comprising a physiologically acceptable excipient and a compound of Formula (I) or any one of the substructures as represented by Formulae (I-1)-(I-14), in an amount effective to inhibit conductance of chloride through a calcium-activated chloride channel, thereby inhibiting fluid secretion from the cell, wherein the subject has a condition, disease or disorder that is treatable by inhibiting conductance of chloride through a calcium-activated chloride channel. In certain embodiments, the disease or disorder is selected from abnormally increased intestinal fluid secretion, secretory diarrhea, asthma, chronic obstructive pulmonary disease, bronchiectasis, or cystic fibrosis. In other embodiments, a condition that is treatable by inhibiting conductance of chloride through a calcium-activated chloride channel includes abnormally increased mucus secretion, which in certain embodiments is a condition of a disease or disorder that is a pulmonary disorder (e.g., asthma, chronic obstructive pulmonary disease, bronchiectasis, or cystic fibrosis). In a specific embodiment, the compound is 2-(2-bromo-2,2-difluoro-acetylamino)-5,6,7,8-tetrahydro-4H-cyclohepta[b]thiophene-3-carboxylic acid o-tolylamide.

In another embodiment, a method of treating a condition, disease, or disorder associated with abnormally increased chloride ion secretion is provided, wherein the method comprises administering to a subject a pharmaceutical composition comprising a physiologically acceptable excipient and a compound of Formula (I) or any one of the substructures as represented by Formulae (I-1)-(I-14), in an amount effective to inhibit a calcium-activated chloride channel, thereby inhibiting chloride ion secretion. In one certain embodiment, the disease or disorder is abnormally (i.e., aberrantly) increased intestinal fluid secretion. In a particular embodiment, the disease or disorder is secretory diarrhea. In another particular embodiment, the condition, which may be a condition of the disease or disorder described herein is abnormally increased mucus secretion. In certain embodiments, a disease or disorder that comprises the condition of abnormally increased mucus secretion is asthma, chronic obstructive pulmonary disease, bronchiectasis, or cystic fibrosis. In certain embodiments, the method of treating a disease or disorder further comprising administering to the subject an agent that inhibits ion transport by a cystic fibrosis transmembrane conductance regulator (CFTR). In a specific embodiment, the compound is 2-(2-bromo-2,2-difluoro-acetylamino)-5,6,7,8-tetrahydro-4H-cyclohepta[b]thiophene-3-carboxylic acid o-tolylamide.

Another embodiment provides a method for reducing pain in a subject in need thereof comprising administering to the subject an effective amount of a pharmaceutical composition comprising a physiologically acceptable excipient and a compound of Formula (I) or any one of the substructures as represented by Formulae (I-1)-(I-14).

Another embodiment provides a method for treating cancer in a subject in need thereof comprising administering to the subject an effective amount of a pharmaceutical composition comprising a physiologically acceptable excipient and a compound of Formula (I) or any one of the substructures as represented by Formulae (I-1)-(I-14). In various embodiments, the cancer may be gastrointestinal stromal, esophageal cancer, PR-positive or HER2-negative breast cancer.

Also provided herein is a use of a composition or a compound of Formula (I) or any one of the substructures as represented by Formulae (I-1)-(I-14), for treating a condition, disease, or disorder associated with abnormally increased chloride ion secretion from a cell. In specific embodiments, the disease or disorder is secretory diarrhea, asthma, chronic obstructive pulmonary disease, bronchiectasis, or cystic fibrosis. In a specific embodiment, the compound is 2-(2-bromo-2,2-difluoro-acetylamino)-5,6,7,8-tetrahydro-4H-cyclohepta[b]thiophene-3-carboxylic acid o-tolylamide.

Also provided herein is a use of a composition or a compound of Formula (I) or any one of the substructures as represented by Formulae (I-1)-(I-14), for reducing or managing pain, or for treating cancer. In a specific embodiment, the compound is 2-(2-bromo-2,2-difluoro-acetylamino)-5,6,7,8-tetrahydro-4H-cyclohepta[b]thiophene-3-carboxylic acid o-tolylamide.

Another embodiment provides use of a composition or a compound of Formula (I) or any one of the substructures as represented by Formulae (I-1)-(I-14), for the manufacture of a medicament for treating a condition, disease, or disorder associated with abnormally increased chloride ion secretion from a cell. In a certain embodiment, the cell is an epithelial cell. In a particular embodiment, the epithelial cell is an intestinal or lung epithelial cell. In specific embodiments, the disease or disorder is secretory diarrhea, asthma, chronic obstructive pulmonary disease, bronchiectasis, or cystic fibrosis. In a specific embodiment, the compound is 2-(2-bromo-2,2-difluoro-acetylamino)-5,6,7,8-tetrahydro-4H-cyclohepta[b]thiophene-3-carboxylic acid o-tolylamide.

EXAMPLES

Abbreviations

AACT, 2-acylamino-cycloalkylthiophene-3-carboxylic acid arylamide; ANO1, anoctamin 1; CaCC, calcium-activated chloride channel; CFTR, cystic fibrosis transmembrane regulator; DCM, dichloromethane; 4-DMAP, N,N-dimethylaminopyridine; DMF, N,N-dimethylformamide; DMSO, dimethyl sulfoxide; EDCI-HCl, 1-(3-dimethylaminopropyl)-3-ethylcarbodiimide hydrochloride; FPR, fluorescent plate reader; FRT, Fischer Rat Thyroid; PBS, phosphate-buffered saline; RT, room temperature; TLC, thin layer chromatography; TMEM16A, transmembrane member 16A; YFP, yellow fluorescent protein.

Unless otherwise indicated, all reaction solvents were anhydrous and obtained as such from commercial sources. Difluoroiodoacetic acid was purchased from Synquest Laboratories (Alachua, Fla.). All other reagents were used as supplied. RP-HPLC analysis was performed using a Dionex Ultimate 3000 system, using a $C_{18}$ column [3×150 mm]. Low resolution ESI-LCMS was carried out with an Agilent 1100 HPLC coupled to an Agilent 1956B MSD. RP-HPLC runs typically employed gradients of two solvents: [A]=$H_2O$ (0.05% TFA) and [B] $CH_3CN$ (0.05% TFA); RP-LCMS used the same solvent system using the modifier formic acid (88% aq). The standard HPLC and LCMS gradients proceeded with [A:B]=95:5 to [A:B]=5:95 over 10 minutes. HRMS was performed using a hybrid quadrupole orbitrap mass analyzer, QExactive (Thermo, Bremen, Germany), with an electrospray ionization source. The mass resolution was set as 70,000 at m/z 200 and the mass accuracy was less than 3 ppm. $^1H$ and $^{13}C$ NMR spectra were recorded on a Bruker 500 MHz instrument. $^1H$ NMR chemical shifts are relative to TMS (δ=0.00 ppm), $CDCl_3$ (δ 7.26), $CD_3OD$ (δ=4.87 and 3.31), acetone-$d_6$ (δ 2.05), or DMSO-$d_6$ (δ 2.5). $^{13}C$ NMR chemical shifts are relative to $CD_3OD$ (δ 49.2) or $CDCl_3$ (δ 77.2).

General procedure 1: substituted cyanoacetamides (2a-2k) prepared from coupling of substituted anilines (1a-1k) with cyanoacetic acid. Substituted aniline (typical scale 6 mmol) (1a-1c) was dissolved in DCM (0.5M), followed by addition of cyanoacetic acid (1.0 eq) and EDCI-HCl (1.2 eq) and was stirred under argon at RT for 1h. LCMS indicated consumption of starting material and formation of product. The mixture was concentrated in vacuo. The crude product was treated with HCl (0.1M aq; 100 ml), transferred to a separatory funnel and extracted with ethyl acetate. The organic phase was then washed with additional HCl (0.1M aq), water, NaCl (satd aq), and was then dried over $Na_2SO_4$ and concentrated in vacuo, to yield the title products (2a-2k) (shown below) typically as a colorless to pink solids:

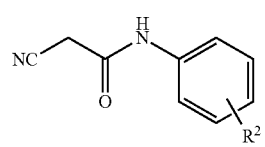

2a-2k

Table 1 shows the synthesis yields for EDCI-mediated cyanoacetamide according to the General procedure 1; yields (%) are of the isolated or purified products. Purity of compounds was >95% based on HPLC-LCMS analysis at 254 nm, and absence of impurities was confirmed by $^1$H NMR spectra.

General procedure 2: 2-aminocycloalkylthiophene-3-carboxylic acid arylamides (5a-5v) prepared in a two step process from cyclic ketones (3a-3d) and substituted cyanoacetamides (2a-2k). Substituted cyanoacetamides (typical scale 3 mmol) (2a-2k) was dissolved in toluene (0.1 M), followed by the addition of the appropriate cyclic ketone (3a-3d) (7.0 eq), ammonium acetate (5.0 eq), glacial acetic acid (7.0 eq), and Na$_2$SO$_4$ (5.0 eq). This reaction mixture was refluxed at 100° C. for 1 h. LCMS indicated consumption of starting material and the formation of the desired Knoevenagel product (4a-4v), as well as excess ketone starting material. The mixture was then cooled to RT and treated with NaHCO$_3$ (5% aq), and transferred into a separatory funnel for extraction of product with ethyl acetate (3×10 ml). The organic mixture was then washed with additional NaHCO$_3$ (5% aq), water, and NaCl (5% aq), and then then dried over Na$_2$SO$_4$ and concentrated in vacuo, to yield the title products (4a-4v) typically as a dark to red orange oils. The identity and purity of the Knoevenagel product was confirmed by LCMS, and the materials were typically used without additional purification or characterization.

Knoevenagel products (4a-4v) (2.674 mmol) were dissolved in ethanol (0.1 M) and treated with molecular octasulfur ("S$_8$") (2.0 eq) and morpholine (3.0 eq). The mixture was refluxed at 90° C. for 5 h. LCMS was used to follow the progress of the reaction. The mixture was then left to cool to RT. Upon reaching RT, the reaction mixture was filtered by using a Buchner funnel, to remove excess precipitated inorganic sulfur materials. The filtrate was then concentrated in vacuo, and the 2-aminocycloalkylthiophene intermediates (5a-5v) (shown below) were isolated as orange to brown solids.

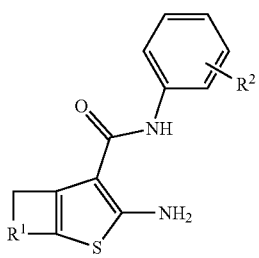

5a-5v

Table 2 shows the synthesis yields for Knoevenagel reaction and subsequent aminothiophene formation reactions. Yields (%) are of the isolated or purified products. Purity of compounds was >95% based on HPLC-LCMS analysis at 254 nm, and absence of impurities was confirmed by $^1$H NMR spectra.

General procedure 3: 2-acylamino-cycloalkylthiophene-3-carboxylic acid arylamides (6aa-6bv; with difluoroiodoacetyl compounds prepared by General Procedure 4) prepared from acylation of 2-aminocycloalkylthiophenes (5a-5v). 2-Aminocycloalkylthiophenes (typically 0.782 mmol) were dissolved in DCM (0.1 M), treated with triethylamine (1.3 eq) and an appropriate acylating agent (e.g. trifluoroacetic anhydride, pentafluoric propionic anhydride, acetic anhydride, propionic anhydride, chlorodifluoroacetic, bromodifluoroacetic, or heptafluorobutyric anhydride) (1.3 eq). The reactions were stirred at RT typically for 10 min, until LCMS confirmed consumption of starting material and formation of product. The mixture was then transferred into a separatory funnel with ethyl acetate. The organic layer was then washed with water, NaCl (satd aq), dried over Na$_2$SO$_4$, and then concentrated in vacuo to yield colorless to light yellow solids (shown below):

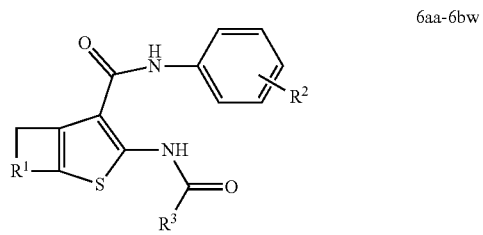

6aa-6bw

Table 3 shows the coupling yields and TMEM16A inhibition of AACT compounds (6aa-6bw). Yields (%) are of the isolated or purified products. IC$_{50}$ (µM) for inhibition of TMEM16A anion conductance using a fluorescence plate reader (FPR) assay. Purity of active compounds was >95% based on HPLC-LCMS analysis at 254 nm, and absence of impurities was confirmed by inspection of $^1$H NMR spectra.

General procedure 4: 2-difluoroiodoacetylamino-cycloalkylthiophene-3-carboxylic acid arylamides (6bn, 6bq, 6bt, 6bw) prepared from EDCI-mediated coupling of 2-aminocycloalkylthiophenes (5) with difluoroiodoacetic acid. 2-Amino-cycloalkylthiophenes (typically 0.164 mmol) were dissolved in 1.6 mL DCM (0.1 M), treated with 4-DMAP (0.1 eq) and iododifluoroacetic acid (1.2 eq), followed by EDCI-HCl (1.5 eq). The reactions were stirred at RT for 60 min, until LCMS confirmed consumption of starting material and formation of product. Reaction mixtures were diluted with ethyl acetate and was washed with HCl (0.1 M aq) (×3) followed by NaCl (satd aq). Organic layers were dried in vacuo and solids were triturated from diethyl ether. The products were isolated as off-white solids.

Example 1

2-(2,2,2-Trifluoro-acetylamino)-5,6,7,8-tetrahydro-4H-cyclohepta[b]thiophene-3-carboxylic acid o-tolylamide (6aa)

Using general procedure 3, 2-aminocycloalkylthiophene (5a) (20 mg, 0.067 mmol) was reacted with trifluoroacetic anhydride to generate the title compound (6aa) as a light brown solid (16 mg, 61%). $^1$H NMR (500 MHz, CDCl$_3$) δ 1.73-1.74 (m, 4H), 1.90 (q, J=5 Hz, 2H), 2.34 (s, 3H), 2.82-2.86 (m, 2H), 3.06 (bs, 2H), 7.13-7.29 (m, 3H), 7.66 (d, J=7 Hz, 1H), 8.60 (bs, 1H), 11.93 (bs, 1H). $^{13}$C NMR (125 MHz, CDCl$_3$) δ 18.1, 27.2, 27.6, 28.8, 29.1, 31.8, 115.6 (q, J=285 Hz), 120.3, 123.2, 126.0, 127.1, 129.2, 133.3, 134.9, 138.9, 153.4 (q, J=39 Hz), 153.7, 164.4. ESI-HRMS m/z calculated for C$_{19}$H$_{19}$F$_3$N$_2$O$_2$S [M+H] 397.1192, found [M+H] 397.1190.

Example 2

2-(2,2,3,3,3-Pentafluoro-propionylamino)-5,6,7,8-tetrahydro-4H-cyclohepta[b]thiophene-3-carboxylic acid o-tolylamide (6ab)

Using general procedure 3, 2-aminocycloalkylthiophene (5a) (20 mg, 0.067 mmol) was reacted with pentafluoropropionic anhydride to generate the title compound (6ab) as a solid (19 mg, 65%). $^1$H NMR (500 MHz, CDCl$_3$) 1.71-1.74 (m, 2H), 1.90-194 (m, 2H), 2.34 (s, 3H), 2.78-2.86 (m, 2H), 3.07-3.10 (m, 2H), 7.16-7.29 (m, 3H), 7.65 (d, J=8 Hz, 1H), 8.56 (bs, 1H), 12.15 (bs, 1H). ESI-LCMS (low resolution) m/z calculated for C$_{20}$H$_{19}$F$_5$N$_2$O$_2$S [M+H] 447.1, found [M+H] 447.2.

Example 3

2-Acetylamino-5,6,7,8-tetrahydro-4H-cyclohepta[b]thiophene-3-carboxylic acid o-tolylamide (6ac)

Using general procedure 3, 2-aminocycloalkylthiophene (5a) (20 mg, 0.067 mmol) was reacted with acetic anhydride to generate the title compound (6ac) as a solid (19 mg, 82%). $^1$H NMR (500 MHz, CDCl$_3$) δ 1.72-1.75 (m, 4H), 1.90-1.92 (m, 2H), 2.19 (s, 3H), 2.31 (s, 3H), 2.78 (t, J=8 Hz, 2H), 2.96 (t, J=8 Hz, 2H), 7.14 (t, J=8 Hz, 1H), 7.25-7.28 (m, 3H), 7.87 (d, J=8 Hz, 1H), 10.87 (bs, 1H), ESI-LCMS (low resolution) m/z calculated for C$_{19}$H$_{22}$N$_2$O$_2$S [M+H] 343.1, found [M+H] 343.2.

Example 4

2-Propionylamino-5,6,7,8-tetrahydro-4H-cyclohepta[b]thiophene-3-carboxylic acid o-tolylamide (6ad)

Using general procedure 3, 2-aminocycloalkylthiophene (5a) (20 mg, 0.067 mmol) was reacted with propionic anhydride to generate the title compound (6ad) as a solid (17 mg, 70%), $^1$H NMR (500 MHz, CDCl$_3$) δ 1.24 (t, J=8 Hz, 3H), 1.72-1.76 (m, 4H), 1.91-1.93 (m, 2H), 2.31 (s, 3H), 2.44 (q, J=8 Hz, 2H), 2.78 (t, J=8 Hz, 2H), 2.95-2.98 (m, 2H), 7.14 (t, J=8 Hz, 1H), 7.25-7.30 (m, 3H), 7.89 (d, J=8 Hz, 1H), 10.91 (bs, 1H). ESI-LCMS (low resolution) m/z calculated for C$_{20}$H$_{24}$N$_2$O$_2$S [M+H] 357.5, found [M+H] 357.3.

Example 5

2-(2,2,2-Trifluoro-acetylamino)-5,6,7,8-tetrahydro-4H-cyclohepta[b]thiophene-3-carboxylic acid phenylamide (6ae)

Using general procedure 3, 2-aminocycloalkylthiophene (5b) (100 mg, 0.349 mmol) was reacted with trifluoroacetic anhydride to generate the title compound (6ae) as a white solid (51 mg, 38%). $^1$H NMR (500 MHz, acetone-d$_6$) δ 1.64-1.70 (m, 4H), 1.86-1.91 (m, 2H), 2.81-2.83 (m, 2H), 2.98 (bs, 2H), 7.09-7.12 (m, 1H), 7.35 (p, J=8 Hz, 2H), 7.61 (d, J=8 Hz, 1H), 7.76 (d, J=8 Hz, 1H), 9.45 (bs, 1H), 11.51 (bs, 1H). ESI-LCMS (low resolution) m/z calculated for C$_{18}$H$_{17}$F$_3$N$_2$O$_2$S [M+H] 382.4, found [M+H] 382.6.

Example 6

2-(2,2,3,3,3-Pentafluoro-propionylamino)-5,6,7,8-tetrahydro-4H-cyclohepta[b]thiophene-3-carboxylic acid phenylamide (6af)

Using general procedure 3, 2-aminocycloalkylthiophene (5b) (25 mg, 0,087 mmol) was reacted with pentafluoropropionic anhydride to generate the title compound (6af) as a light-brown solid (37 mg, 97%). $^1$H NMR (500 MHz, acetone-d$_6$) δ 1.61-1.68 (m, 4H), 1.86-1.88 (m, 2H), 2.72-2.75 (m, 2H), 2.83-2.86 (m, 2H), 7.12 (t, J=6 Hz, 1H), 7.2-7.37 (m, 2H), 7.61 (d, J=8 Hz, 1H), 7.76 (d, J=8 Hz, 1H), 9.00 (bs, 1H), 10.14 (bs, 1H). ESI-LCMS (low resolution) m/z calculated for C$_{19}$H$_{17}$F$_5$N$_2$O$_2$S [M+H] 433.4, found [M+H] 433.

Example 7

2-Acetylamino-5,6,7,8-tetrahydro-4H-cyclohepta[b]thiophene-3-carboxylic acid phenylamide (6ag)

Using general procedure 3, 2-aminocycloalkylthiophene (5b) (25 mg, 0.087 mmol) was reacted with acetic anhydride to generate the title compound (6ag) as a yellow solid (22 mg, 80%). $^1$H NMR (500 MHz, acetone-d$_6$) δ 1.61-1.68 (m, 4H), 1.86-1.88 (m, 2H), 2.72-2.75 (m, 2H), 2.83-2.86 (m, 2H), 7.12 (t, J=6 Hz, 1H), 7.32-7.37 (m, 2H), 7.61 (d, J=8 Hz, 1H), 7.76 (d, J=8 Hz, 1H), 9.00 (bs, 1H), 10.14 (bs, 1H). ESI-LCMS (low resolution) m/z calculated for C$_{17}$H$_{18}$N$_2$O$_2$S [M+H] 315.4, found [M+H] 315.6.

Example 8

2-Propionylamino-5,6,7,8-tetrahydro-4H-cyclohepta[b]thiophene-3-carboxylic acid phenylamide (6ah)

Using general procedure 3, 2-aminocycloalkylthiophene (5b) (25 mg, 0.087 mmol) was reacted with propionic anhydride to generate the title compound (6ah) as a white powder (26 mg, 87%). $^1$H NMR (500 MHz, acetone-d$_6$) δ 1.16 (t, J=7 Hz, 3H), 1.64-1.67 (m, 4H), 1.84-1.86 (m, 2H), 2.44 (q, J=8 Hz, 2H), 2.72-2.75 (m, 2H), 2.83-2.86 (m, 2H), 7.12 (t, J=7 Hz, 1H), 7.36 (t, J=8 Hz, 2H), 7.76 (d, J=8 Hz, 2H), 8.99 (bs, 1H), 10.14 (bs, 1H). ESI-LCMS (low resolution) m/z calculated for C$_{19}$H$_{22}$N$_2$O$_2$S [M+H] 343.4, found [M+H] 343.6.

Example 9

2-(2,2,2-Trifluoro-acetylamino)-5,6,7,8-tetrahydro-4H-cyclohepta[b]thiophene-3-carboxylic acid (2-ethyl-phenyl)-amide (6ai)

Using general procedure 3, 2-aminocycloalkylthiophene (5c) (165 mg, 0.527 mmol) was reacted with trifluoroacetic anhydride to generate the title compound (6ai) as an off-white solid (3.0 mg, 7%). $^1$H NMR (500 MHz, CDCl$_3$) δ 1.26 (t, J=7 Hz, 3H), 1.54 (m, 2H), 1.76 (m, 2H). 1.93 (m, 2H), 2.64 (q, J=7 Hz, 2H), 2.82-2.84 (m, 2H), 2.98-3.01 (m, 2H), 7.21 (t, J=7 Hz, 1H), 7.27 (m, 2H), 7.85 (d, J=7 Hz, 1H). $^{13}$C NMR (125 MHz, CDCl$_3$) δ 14.2, 24.5, 27.2, 28.8, 29.1, 31.7, 124.1, 126.4, 126.9, 128.9, 133.2, 134.1, 134.9, 135.4. ESI-LCMS (low resolution) m/z calculated for C$_{20}$H$_{21}$F$_3$N$_2$O$_2$S [M+H] 411.5, found [M+H] 411.5.

Example 10

2-(2,2,2-Trifluoro-acetylamino)-5,6,7,8-tetrahydro-4H-cyclohepta[b]thiophene-3-carboxylic acid (2-fluoro-phenyl)-amide (6aj)

Using general procedure 3, 2-aminocycloalkylthiophene (5d) (69 mg, 0.227 mmol) was reacted with trifluoroacetic anhydride to generate the title compound (6aj) as an off-white, slightly orange solid substance (43.3 mg, 48%). $^1$H NMR (500 MHz, CDCl$_3$) δ 1.75-1.83 (m, 4H) 1.90-1.97 (m, 2H), 2.82-2.85 (m, 2H), 2.97-3.02 (m, 2H), 7.12-7.25 (m, 3H), 7.7 (bs, 1H), 8.4 (t, J=7 Hz, 1H). $^{13}$C NMR (125 MHz, CDCl$_3$) δ 26.8, 27.4, 28.7, 31.5, 114.8 (d, J=20 Hz), 120.1, 122.1, 124.8 (d, J=4 Hz), 125.0 (d, J=8 Hz), 125.7, 133.3, 134.9, 151.8, 153.4, 153.7, 164.0. ESI-LCMS (low resolution) m/z calculated for C$_{18}$H$_{16}$F$_4$N$_2$O$_2$S [M+H] 400.4, found [M+H] 401.0.

Example 11

2-(2,2,2-Trifluoro-acetylamino)-5,6,7,8-tetrahydro-4H-cyclohepta[b]thiophene-3-carboxylic acid (4-fluoro-phenyl)amide (6ak)

Using general procedure 3, 2-aminocycloalkylthiophene (5e) (250 mg, 0.821 mmol) was reacted with trifluoroacetic anhydride to generate the title compound (6ak) as white solid (197 mg, 60%). $^1$H NMR (500 MHz, CDCl$_3$) δ 1.77-1.78 (m, 4H), 1.91-1.94(m, 2H), 2.82-2.84(m, 2H), 2.96-2.98 (m, 2H), 7.90 (d, J=8 Hz, 2H), 7.52 (d, J=8 Hz, 2H), 12.00 (bs, 1H). $^{13}$C NMR (125 MHz, CDCl$_3$) δ 27.4, 27.7, 29.0, 29.3, 31.8, 114.7, 116.2 (d, J=22 Hz), 120.5, 122.8 (d, J=8 Hz), 132.9, 133.3, 135.3, 139.0, 153.8 (q, J=39 Hz), 161.2, 164.4. ESI-HRMS m/z calculated for C$_{18}$H$_{16}$F$_4$N$_2$O$_2$S [M+H] 401.0942, found [M+H] 401.0942.

Example 12

2-(2,2,2-Trifluoro-acetylamino)-5,6,7,8-tetrahydro4H-cyclohepta[b]thiophene-3-carboxylic acid (2-chloro-phenyl)-amide (6al)

Using general procedure 3, 2-aminocycloalkylthiophene (5f) (89 mg, 0.279 mmol) was reacted with trifluoroacetic anhydride to generate the title compound (6al) as a light brown powder (101 mg, 87%). $^1$H NMR (500 MHz, CDCl$_3$) δ 1.69-1.76 (m, 4H), 1.93-1.95 (m, 2H), 2.92-2.94 (m, 2H), 3.21-3.23 (m, 2H), 7.20 (t, J=8 Hz, 1H), 7.36 (t, J=8 Hz, 1H), 7.45 (d, J=8 HZ, 1H), 8.32 (d, J=8 Hz, 1H), 8.42 (bs, 1H), 12.2 (bs, 1H). ESI-HRMS m/z calculated for C$_{18}$H$_{16}$ClF$_3$N$_2$O$_2$S [M−H] 415.0500, found [M−H] 415.0497.

Example 13

2-(2,2,3,3,3-Pentafluoro-propionylamino)-5,6,7,8-tetrahydro-4H-cyclohepta[b]thiophene-3-carboxylic acid (2-chloro-phenyl)-amide (6 am)

Using general procedure 3, 2-aminocycloalkylthiophene (5f) (70 mg 0.218 mmol) was reacted with pentafluoropropionic anhydride to generate the title compound (6 am) as a white solid (92 mg, 91%). $^1$H NMR (500 MHz, CDCl$_3$) δ 1.77-1.80 (m, 4H), 1.93-1.96 (bs, 2H), 2.84-2.86 (m, 2H), 3.00-3.10 (m, 2H), 7.13 (t, J=7 Hz, 1H), 7.31 (t, J=8 Hz, 1H), 7.43 (d, J=7 Hz, 1H), 8.05 (bs, 1H), 8.53 (d, J=7 Hz, 1H), 12.27 (bs, 1H). ESI-HRMS m/z calculated for C$_{19}$H$_{16}$ClF$_5$N$_2$O$_2$S [M−H] 465.0468, found [M−H] 465.0463.

Example 14

2-(2,2,2-Trifluoro-acetylamino)-5,6,7,8-tetrahydro-4H-cyclohepta[b]thiophene-3-carboxylic acid (3-chloro-phenyl)-amide (6an)

Using general procedure 3, 2-aminocycloalkylthiophene (5g) (224 mg, 0.698 mmol) was reacted with trifluoroacetic anhydride to generate the title compound (6an) as a beige solid (66 mg, 23%). $^1$H NMR (500 MHz, CDCl$_3$) δ 1.76-1.78 (m, 4H), 1.92-1.94 (m, 2H), 2.83-2.84 (m, 2H), 2.95-2.98 (m, 2H), 7.18 (d, J=8 Hz, 1H), 7.32 (t, J=8 Hz, 1H), 7.41 (d, J=7 Hz, 1H), 7.67 (bs, 1H). ESI-LCMS (low resolution) m/z calculated for C$_{18}$H$_{16}$CH$_3$N$_2$O$_2$S [M+H] 417.9, found [M+H] 417.5.

Example 15

2-(2,2,2-Trifluoro-acetylamino)-5,6,7,8-tetrahydro-4H-cyclohepta[b]thiophene-3-carboxylic acid (4-chloro-phenyl)-amide (6ao)

Using general procedure 3, 2-aminocycloalkylthiophene (5h) (110 mg, 0.343 mmol) was reacted with trifluoroacetic anhydride to generate the title compound (6ao) as a white solid (6 mg, 4%). $^1$H NMR (500 MHz, CDCl$_3$) δ 1.77-1.79 (m, 4H), 1.93-1.95 (m, 2H), 2.83-2.85 (m, 2H), 2.95-2.98 (m, 2H), 7.36 (d, J=7 Hz, 2H), 7.51 (d, J=7 Hz, 2H), 11.96 (bs, 1H). ESI-LCMS (low resolution) m/z calculated for C$_{18}$H$_{16}$ClF$_3$N$_2$O$_2$S [M+H] 417.8, found [M+H] 417.3.

Example 16

2-(2,2,2-Trifluoro-acetylamino)-5,6,7,8-tetrahydro-4H-cyclohepta[b]thiophene-3-carboxylic acid (4-trifluoromethyl-phenyl)-amide (6ap)

Using general procedure 3, 2-aminocycloalkylthiophene (5i) (275 mg, 0.776 mmol) was reacted with trifluoroacetic anhydride to generate the title compound (6ap) as a light-yellow solid (49 mg, 1.7%). $^1$H NMR (500 MHz, CD$_3$OD): δ 1.65-1.68 (m, 2H), 1.70-1.73 (m, 2H), 1.89-1.92 (m, 2H), 2.81-2.83 (m, 4H), 7.63 (s, 1H), 7.64 (d, J=9 Hz, 2H), 7.83 (d, J=9 Hz, 2H). $^{13}$C NMR (125 MHz, CD$_3$OD) δ 28.8, 29.3, 29.6, 30.3, 33.6, 121.4, 127.1, 127.2, 155.1, 156.8, 168.1. ESI-HRMS m/z calculated for C$_{19}$H$_{16}$F$_6$N$_2$O$_2$S [M−H] 449.0794, found [M−H] 449.0762.

Example 17

2-(2,2,2-Trifluoro-acetylamino)-5,6,7,8-tetrahydro-4H-cyclohepta[b]thiophene-3-carboxylic acid (2-trifluoromethoxy-phenyl)-amide (6aq)

Using general procedure 3, 2-aminocycloalkylthiophene (5j) (25 mg, 0.067 mmol) was reacted with trifluoroacetic anhydride to generate the title compound (6aq) as a brown solid (3.8 mg, 12%). $^1$H NMR (500 MHz, CDCl$_3$) δ 1.76-1.79 (m, 4H), 1.80-1.96 (m, 2H), 2.83-2.87 (m, 2H), 2.99-3.00 (m, 2H), 7.18-7.21 (m, 1H), 7.38-7.39 (m, 2H), 7.84 (bs, 1H), 8.56 (t, J=7 Hz, 1H), 12.18 (bs, 1H). ESI-LCMS (low resolution) m/z calculated for C$_{19}$H$_{16}$F$_6$N$_2$O$_3$S [M+H] 467.4, found [M+H] 467.3.

Example 18

2-(2,2,3,3,3-Pentafluoro-propionylamino)-5,6,7,8-tetrahydro-4H-cyclohepta[b]thiophene-3-carboxylic acid (2-trifluoromethoxy-phenyl)-amide (6ar)

Using general procedure 3, 2-aminocycloalkylthiophene (5j) (25 mg, 0.067 mmol) was reacted with pentafluoropropionic anhydride to generate the title compound (6aq) as a light red solid (10 mg, 30%). $^1$H NMR (500 MHz, acetone-d$_6$) δ 1.77-1.79 (m, 4H), 1.94 (bs, 2H), 2.83 (bs, 2H), 2.98-3.00 (m, 2H), 7.18-7.20 (m, 1H), 7.33-7.39 (m, 2H), 7.85 (bs, 1H), 8.55 (d, J=8 Hz, 1H), 12.33 (bs, 1H), ESI-LCMS (low resolution) m/z calculated for $C_{20}H_{16}F_8N_2O_3S$ [M+H] 517.4, found [M+H] 517.4.

Example 19

2-Acetylamino-5,6,7,8-tetrahydro-4H-cyclohepta[b]thiophene-3-carboxylic acid (2-trifluoromethoryphenyl)-amide (6as)

Using general procedure 3, 2-aminocycloalkylthiophene (5j) (25 mg, 0.067 mmol) was reacted with acetic anhydride to generate the title compound (6as) as brown solid (15 mg, 55%). $^1$H NMR (500 MHz, acetone-$d_6$) δ 1.70-1.77 (m, 4H), 1.93 (bs, 2H), 2.19 (bs, 3H), 2.79 (bs, 2H), 2.95-2.98 (m, 2H), 7.20 (t, J=7 Hz, 1H), 7.35-7.39 (m, 2H), 7.72 (bs, 1H), 8.52 (d, J=8 Hz, 1H), 10.82 (bs, 1H). ESI-LCMS (low resolution) m/z calculated for $C_{19}H_{19}F_3N_2O_3S$ [M+H] 413.4, found [M+H] 413.1.

Example 20

2-Propionylamino-5,6,7,8-tetrahydro-4H-cyclohepta[b]thiophene-3-carboxylic acid (2-trifluoromethoryphenyl)amide (6at)

Using general procedure 3, 2-aminocycloalkylthiophene (5j) (25 mg, 0.067 mmol) was reacted with propionic anhydride to generate the title compound (6at) as a brown solid (14 mg, 50%). $^1$H NMR (500 MHz, acetone-$d_6$) δ 1.74-1.76 (m, 4H), 1.89-1.91 (m, 2H), 2.75-2.88 (m, 2H), 2.93-2.96 (m, 2H), 7.16 (t, J=7 Hz, 1H), 7.32-7.37 (m, 2H), 7.71 (bs, 1H), 8.51 (d, J=8 Hz, 1H), 10.97 (bs, 1H). ESI-LCMS (low resolution) m/z calculated $C_{20}H_{21}F_3N_2O_3S$ [M+H] 427.4, found [M+H] 427.3.

Example 21

2-(2,2,2-Trifluoro-acetylamino)-4,5,6,7-tetrahydro-benzo[b]thiophene-3-carboxylic acid phenylamide (6au)

Using general procedure 3, 2-aminocycloalkylthiophene (5k) (1.2 g, 4.391 mmol) was reacted with trifluoroacetic anhydride to generate the title compound (6au) as a brown solid (1.5 g, 93%). $^1$H NMR (500 MHz, CDCl$_3$) δ 1.92-1.96 (m, 4H), 2.77-2.79 (m, 2H), 2.90-2.91 (m, 2H), 7.21 (t, J=7 Hz, 1H), 7.40 (t, J=8 Hz, 2H), 7.56 (d, J=9 Hz, 2H), 7.71 (bs, 1H), 13.19 (bs, 1H). ESI-LCMS (low resolution) m/z calculated for $C_{17}H_{15}F_3N_2O_2S$ [M+H] 369.1, found [M+H] 369.5.

Example 22

2-(2,2,2-Trifluoro-acetylamino)-4,5,6,7-tetrahydro-benzo[b]thiophene-3-carboxylic acid o-tolylamide (6av)

Using general procedure 3, 2-aminocycloalkylthiophene (5l) (80 mg 0.279 mmol) was reacted with trifluoroacetic anhydride to generate the title compound (6av) as a brown solid (18 mg, 17%). $^1$H NMR (500 MHz, CDCl$_3$) δ 1.92-1.97 (m, 4H), 2.35 (s, 3H), 2.79-2.80 (m, 2H), 2.91-2.93 (m, 2H), 7.18 (t, J=8 Hz, 1H), 7.28-7.30 (m, 2H), 7.56 (bs, 1H), 7.82 (d, J=8 Hz, 1H), 13.29 (bs, 1H). ESI-HRMS m/z calculated for $C_{18}H_{17}F_3N_2O_2S$ [M−H] 381.0890, found [M−H] 381.0888.

Example 23

2-(2,2,2-Trifluoro-acetylamino)-4,5,6,7-tetrahydro-benzo[b]thiophene-3-carboxylic acid p-tolylamide (6aw)

Using general procedure 3, 2-aminocycloalkylthiophene (5m) (24 mg, 0.349 mmol) was reacted with trifluoroacetic anhydride to generate the title compound (6aw) as a white solid (10 mg, 30%). $^1$HNMR (500 MHz, CDCl$_3$) δ 1.91-1.95 (m, 4H), 2.37 (s, 3H), 2.77-2.79 (m, 2H), 2.89-2.91 (m, 2H), 7.20 (d, J=8 Hz, 2H), 7.43 (d, J=8 Hz, 2H), 7.65 (bs, 1H), 13.24 (bs, 1H). ESI-LCMS (low resolution) m/z calculated for $C_{38}H_{17}F_3N_2O_2S$ [M+H] 383.4, found [M+H] 383.5.

Example 24

2-(2,2,2-Trifluoro-acetylamino)-4,5,6,7-tetrahydro-benzo[b]thiophene-3-carboxylic acid (4-fluoro-phenyl)-amide (6ax)

Using general procedure 3, 2-aminocycloalkylthiophene (5n) (87 mg, 0.689 mmol) was reacted with trifluoroacetic anhydride to generate the title compound (6ax) as a white solid (55 mg, 48%). $^1$H NMR (500 MHz, CDCl$_3$) δ 1.91-1.95 (m, 4H), 2.77-2.79 (m, 2H), 2.86-2.91 (m, 2H) 7.07-7.11 (m, 2H), 7.51-7.53 (m, 2H), 7.66 (bs, 1H), 13.16 (bs, 1H). $^{13}$C NMR NMR (125 MHz, CDCl$_3$) δ 22.7, 23.0, 24.7, 27.0, 116.2 (d, J=22 Hz), 116.9, 117.0, 123.3, 127.3, 131.0, 132.8, 154.1 (q, J=38 Hz), 159.3, 161.3, 164.5. ESI-HRMS m/z calculated for $C_{17}H_{14}F_4N_2O_2S$ [M+H]/385.0639, found [M−H] 385.0638.

Example 25

2-(2,2,3,3,3-Pentafluoro-propionylamino)-4,7-dihydro-5H-thieno[2,3-c]pyran-3-carboxylic acid o-tolylamide (6ay)

Using general procedure 3, 2-aminocycloalkylthiophene (5o) (20 mg, 0.069 mmol) was reacted with pentafluoropropionic anhydride to generate the title compound (6ay) as a white solid (2 mg, 6%). $^1$H NMR (500 MHz, CDCl$_3$) δ 2.34 (s, 3H), 3.01-3.03 (m, 2H), 4.08 (t, J=5 Hz, 2H), 4.83 (s, 2H), 7.18-7.21 (m, 2H), 7.29-7.32 (1H), 7.45 (bs, 1H), 7.8 (d, J=8 Hz, 1H), 13.39 (bs, 1H). ESI-LCMS (low resolution) m/z calculated for $C_{18}H_{15}F_5N_2O_3S$ [M+H] 435.1 found [M+H] 435.1.

Example 26

2-Propionylamino-4,7-dihydro-5H-thieno[2,3-c]pyran-3-carboxylic acid o-tolylamide (6az)

Using general procedure 3, 2-aminocycloalkylthiophene (5o) (20 mg, 0.069 mmol) was reacted with propionic anhydride to generate the title compound (6az) as a brown solid (10 mg, 40%). $^1$H NMR (500 MHz, CDCl$_3$) δ 1.19 (t, 3H, J=7 Hz), 2.53 (q, 2H, J=7 Hz), 3.07-3.08 (m, 2H), 3.97 (t, 2H, J=6 Hz), 4.74 (s, 2H), 7.15 (t, 1H, J=8 Hz), 7.23 (t, 1H, J=8 Hz), 7.27 (d, 1H, J=8 Hz), 7.72 (d, 1H, J=8 Hz), 8.20 (bs, 1H). ESI-LCMS (low resolution) m/z calculated for $C_{18}H_{20}N_2O_3S$ [M+H] 345.1, found [M+H] 345.0.

Example 27

2-(2,2,2-Trifluoro-acetylamino)-4,7-dihydro-5H-thieno[2,3-c]pyran-3-carboxylic acid (2-chloro-phenyl)-amide (6ba)

Using general procedure 3, 2-aminocycloalkylthiophene (5p) (500 mg, 0.085 mmol) was reacted with trifluoroacetic anhydride to generate the title compound (6ba) as a brown solid (175 mg, 67%). $^1$H NMR (500 MHz, acetone-$d_6$) δ 3.10-3.12 (m, 2H), 4.04-4.13 (m, 2H), 4.78-4.86 (m, 2H), 7.11-7.16 (m, 1H), 7.31-7.46 (m, 2H), 8.19 (bs, 1H), 8.45-8.49 (m, 1H), 13.14 (bs, 1H). ESI-LCMS (low resolution) m/z calculated for $C_{16}H_{12}ClF_3N_2O_3S$ [M+H] 405.8, found [M+H] 405.8.

Example 28

2-(2,2,2-Trifluoro-acetylamino)-4,7-dihydro-5H-thieno[2,3-c]pyran-3-carboxylic acid p-tolylamide (6bb)

Using general procedure 3, 2-aminocycloalkylthiophene (5q) (100 mg, 0.694 mmol) was reacted with trifluoroacetic anhydride to generate the title compound (6bb) as a yellow solid (50 mg, 38%). $^1$H NMR (500 MHz, CDCl$_3$) δ 2.37 (s, 3H), 3.00 (t, J=5 Hz, 2H), 4.07 (t, J=5 Hz, 2H), 4.81 (s, 2H), 7.21 (d, J=8 Hz, 2H), 7.42. (d, J=9 Hz, 2H), 7.51 (bs, 1H). ESI-LCMS (low resolution) m/z calculated for $C_{17}H_{15}F_3N_2O_3S$ [M+H] 385.1, found [M+H] 385.3.

Example 29

2-(2,2,2-Trifluoro-acetylamino)-4,7-dihydro-5H-thieno[2,3-c]pyran-3-carboxylic acid (4-fluoro-phenyl)amide (6bc)

Using general procedure 3, 2-aminocycloalkylthiophene (5r) (100 mg, 0.342 mmol) was reacted with trifluoroacetic anhydride to generate the title compound (6bc) as a brown solid (1.8 mg, 13%). $^1$H NMR (500 MHz, CDCl$_3$) δ 3.15 (t, J=5 Hz, 2 h), 4.03 (t, J=5 Hz, 2H), 4.85 (s, 2H), 7.06 (t, J=8 Hz, 2H), 7.21 (d, J=5 Hz, 2H). ESI-HRMS m/z calculated for $C_{16}H_{12}F_4N_2O_3S$ [M−H] 387.0432, found [M−H] 387.0431.

Example 30

2-(2,2,2-Trifluoro-acetylamino)-5,6-dihydro-4H-cyclopenta[b]thiophene-3-carboxylic acid o-tolylamide (6bd)

Using general procedure 3, 2-aminocycloalkylthiophene (5s) (50 mg, 0.184 mmol) was reacted with trifluoroacetic anhydride to generate the title compound (6bd) as a brown solid (7 mg, 10%). $^1$H NMR (500 MHz, CDCl$_3$) δ 2.38 (s, 3H), 2.55-2.58 (m, 2H), 2.96-2.99 (m, 2H), 3.25-3.27 (m, 2H), 7.26-7.28 (m, 3H), 7.84 (bs, 1H), 8.08 (bs, 1H), 13.37 (bs, 1H). ESI-LCMS (low resolution) m/z calculated for $C_{17}H_{15}F_3N_2O_2S$ [M+H] 369.1, found [M+H] 369.0.

Example 31

2-(2,2,3,3,3-Pentafluoro-propionylamino)-5,6-dihydro-4H-cyclopenta[b]thiophene-3-carboxylic acid o-tolylamide (6be)

Using general procedure 3, 2-aminocycloalkylthiophene (5s) (25 mg, 0.092 mmol) was reacted with pentafluoropropionic anhydride to generate the title compound (6be) as an orange solid (14 mg, 37%). $^1$H NMR (500 MHz, CDCl$_3$) δ 2.35 (s, 3H), 2.62 (q, J=7 Hz, 2H), 2.97-3.00 (m, 2H), 3.10 (t, J=7 Hz, 2H), 7.17 (t, J=7 Hz, 1H), 7.26-7.3 (m, 2H), 7.50 (bs, 1H), 7.93 (d, J=8 Hz, 1H), 13.34 (bs, 1H). ESI-LCMS (low resolution) m/z calculated for $C_{18}H_{15}F_5N_2O_2S$ [M+H] 419.1, found [M+H] 419.2.

Example 32

2-Acetylamino-5,6-dihydro-4H-cyclopenta[b]thiophene-3-carboxylic acid o-tolylamide (6bf)

Using general procedure 3, 2-aminocycloalkylthiophene (5s) (50 mg, 0.184 mmol) was reacted with acetic anhydride to generate the title compound (6bf) as a brown solid (22 mg, 38%). $^1$H NMR (500 MHz, CDCl$_3$) δ 2.23 (s, 3H), 2.37 (s, 3H), 2.53 (p, J=8 Hz, 2H), 2.90 (t, J=7 Hz, 2H), 3.20 (t, J=8 Hz, 2H), 7.13 (t, J=8 Hz, 1H), 7.24-7.28 (m, 2H), 7.90 (d, J=8 Hz, 1H), 11.84 (bs, 1H). ESI-LCMS (low resolution) m/z calculated for $C_{17}H_{18}N_2O_2S$ [M+H] 315.1, found [M+H] 315.2.

Example 33

2-Propionylamino-5,6-dihydro-4H-cyclopenta[b]thiophene-3-carboxylic acid o-tolylamide (6bg)

Using general procedure 3, 2-aminocycloalkylthiophene (5s) (50 mg, 0.184 mmol) was reacted with propionic anhydride to generate the title compound (6bg) as a brown solid (20 mg, 33%). $^1$H NMR (500 MHz, CDCl$_3$) δ 1.21 (t, J=8 Hz, 3H), 2.37 (s, 3H), 2.50-2.54 (m, 4H), 2.90 (t, J=7 Hz, 2H), 3.20 (t, J=7 Hz, 2H), 7.12 (t, J=7 Hz, 1H), 7.23-7.27 (m, 2H), 7.89 (d, J=8 Hz, 1H), 11.91 (bs, 1H). ESI-LCMS (low resolution) m/z calculated for $C_{18}H_{20}N_2O_2S$ [M+H] 329.1, found [M+H] 329.3.

Example 34

2-(2,2,2-Trifluoro-acetylamino)-5,6-dihydro-4H-cyclopenta[b]thiophene-3-carboxylic acid p-tolylamide (6bh)

Using general procedure 3, 2-aminocycloalkylthiophene (5t) (35 mg, 0.129 mmol) was reacted with trifluoroacetic anhydride to generate the title compound (6bh) as a brown solid (36 mg, 77%). $^1$H NMR (500 MHz, CDCl$_3$) δ 2.36 (s, 3H), 2.58-2.60 (m, 2H), 2.96-2.98 (m, 2H), 3.09-3.11 (m, 2H) 7.20 (d, J=8 Hz, 2H), 7.45 (d, J=8 Hz, 2H), 7.62 (bs, 1H), 13.15 (bs, 1H). ESI-LCMS (low resolution) m/z calculated for $C_{17}H_{15}F_3N_2O_2S$ [M+H] 369.4, found [M+H] 369.0.

Example 35

2-(2,2,2-Trifluoro-acetylamino)-5,6-dihydro-4H-cyclopenta[b]thiophene-3-carboxylic acid (2-chloro-phenyl)-amide (6bi)

Using general procedure 3, 2-aminocycloalkylthiophene (5u) (25 mg, 0,085 mmol) was reacted with trifluoroacetic anhydride to generate the title compound (6bi) as a light brown solid (21 mg, 64%). $^1$H NMR (500 MHz, CDCl$_3$) δ 2.57-2.63 (m, 2H), 2.94-3.00 (m, 2H), 3.15-3.20 (m, 2H), 7.12 (d, J=8 Hz, 1H), 7.34-7.45 (m, 2H), 8.28 (bs, 1H), 8.50-8.54 (m, 1H). ESI-LCMS (low resolution) m/z calculated for $C_{16}H_{12}ClF_3N_2O_2S$ [M+H] 389.8, found [M+H] 389.7.

Example 36

2-(2,2,2-Trifluoro-acetylamino)-5,6-dihydro-4H-cyclopenta[b]thiophene-3-carboxylic acid (2-trifluoromethoxy-phenyl)-amide (6bj)

Using general procedure 3, 2-aminocycloalkylthiophene (5v) (100 mg, 0.292. mmol) was reacted with trifluoroacetic anhydride to generate the title compound (6bj) as light yellow solid (115 mg, 90%). $^1$H NMR (500 MHz, CDCl$_3$) δ 2.60 (p, J=7 Hz, 1H), 2.96 (t, J=7 Hz, 2H), 3.07 (t, J=7 Hz, 2H), 7.17 (t, J=7 Hz, 2H), 7.30-7.36 (m, 2H), 8.15 (bs, 1H), 8.54 (d, J=7 Hz, 1H), 13.00 (bs, 1H). ESI-LC MS (low resolution) m/z calculated for $C_{17}H_{12}F_6N_2O_3S$ [M+H] 438.3, found [M+H] 438.3.

Example 37

2-(2-Chloro-2,2-difluoro-acetylamino)-5,6,7,8-tetrahydro-4H-cyclohepta[b]thiophene-3-carboxylic acid o-tolylamide (6bk)

Using general procedure 3, 2-aminocycloalkylthiophene (5a) (200 mg, 0.666 mmol) was reacted with chlorodifluoroacetyl chloride to generate the title compound (6bk) as a colorless solid (73 mg, 27%). $^1$H NMR (500 MHz, DMSO-d$_6$): δ 1.62 (bs, 4H), 1.83 (bs, 2H), 2.23 (s, 3H), 2.78 (bs, 4H), 7.11-7.13 (t, J=7 Hz, 1H), 7.17-7.23 (m, 2H), 7.51 (s, 1H), 11.66 (bs, 1H). $^{13}$C NMR (125 MHz, CDCl$_3$) δ 17.9, 27.0, 27.6, 28.5, 31.6, 125.6, 125.7, 130.2, 132.5, 135.9, 136.8, 162.7. ESI-HRMS m/z calculated for $C_{19}H_{19}ClF_2N_2O_2S$ [M–H] 411.0751, found [M–H] 411.0751.

Example 38

2-(2,2,3,3,4,4,4-Heptafluoro-butyrylamino)-5,6,7,8-tetrahydro-4H-cyclohepta[b]thiophene-3-carboxylic acid o-tolylamide (6bl)

Using general procedure 3, 2-aminocycloalkylthiophene (5a) (50 mg, 0.166 mmol)) was reacted with heptafluorobutyric anhydride to generate the title compound (6bl) as an off-white solid (51 mg, 61%). $^1$H NMR (500 MHz, acetone-d$_6$): δ 1.71-1.74 (m, 4H), 1.87-1.91 (m, 2H), 2.33 (s, 3H), 2.82 (bs, 2H), 3.12 (bs, 2H), 7.14 (bs, 1H), 7.21 (t, J=7 Hz, 1H), 7.26 (d, J=7 Hz, 1H), 7.66 (d, J=7 Hz, 1H), 12.19 (bs, 1H). $^{13}$C NMR (125 MHz, CDCl$_3$) δ 18.1, 27.1, 27.5, 28.9, 29.1, 31.8, 120.4, 123.2, 126.0, 126.5, 127.1, 129.2, 130.8, 130.9, 133.3, 134.9, 134.9, 139.0, 153.8, 154.0, 164.3. ESI-HRMS m/z calculated for $C_{21}H_{19}F_7N_2O_2S$ [M–H] 495.0982, found [M–H] 495.0983.

Example 39

2-(2-Bromo-2,2-difluoro-acetylamino)-5,6,7,8-tetrahydro-4H-cyclohepta[b]thiophene-3-carboxylic acid o-tolylamide (6bm)

Using general procedure 3, 2-aminocycloalkylthiophene (5a) (50 mg, 0.166 mmol) was reacted with bromodifluoroacetyl chloride to generate the title compound (6bm) as an off-white solid (28 mg, 36%). $^1$H NMR (500 MHz, CDCl$_3$) δ 1.75-1.78 (m, 4H), 1.92-1.96 (m, 2H), 2.32 (s, 3H), 2.83-2.84 (m, 2H), 3.00-3.02 (m, 2H), 7.16-7.18 (m, 1H), 7.25-7.31 (m, 2H), 7.91 (d, J=7 Hz, 1H), 12.08 (bs, 1H). $^{13}$C NMR (125 MHz, CDCl$_3$) δ 18.0, 27.1, 27.5, 28.8, 29.1, 31.7, 111.0 (t, J=313 Hz), 120.3, 123.1, 125.9, 127.0, 129.1, 130.8, 133.4, 134.8, 134.9, 139.1, 156.3 (t, J=29 Hz), 164.3. ESI-HRMS m/z calculated for $C_{19}H_{19}BrF_2N_2O_2S$ [M–H] 455.0246, found [M–H] 455.0244.

Example 40

2-(2,2-Difluoro-2-iodo-acetylamino)-5,6,7,8-tetrahydro-4H-cyclohepta[b]thiophene-3-carboxylic acid o-tolylamide (6bn)

Using general procedure 4, 2-aminocycloalkylthiophene (5a) (25.0 mg, 0.083 mmol) was reacted with difluoroiodoacetic acid to generate the title compound (6bn) as an off-white solid (28 mg, 67%). $^1$H NMR (500 MHz, CDCl$_3$) δ 1.71-1.80 (m, 4H), 1.89-1.96 (m, 2H), 2.32 (s, 3H), 2.84 (t, 2H, J=6 Hz), 3.01 (t, 2H, J=6 Hz), 7.10-7.35 (m, 3H), 7.92 (d, 1H, J=8 Hz), 11.98 (s, 1H). $^{13}$C NMR (125 MHz, CDCl$_3$) δ 18.0, 27.2, 27.6, 28.8, 29.2, 31.8, 89.6, 120.3, 123.1, 125.9, 126.5, 127.1, 129.1, 130.8, 133.4, 134.8, 134.9, 139.2, 164.3. ESI-HRMS m/z calculated for $C_{19}H_{19}F_2IN_2O_2S$ [M–H] 503.0107, found [M–H] 503.0107.

Example 41

2-(2-Chloro-2,2-difluoro-acetylamino)-5,6,7,8-tetrahydro-4H-cyclohepta[b]thiophene-3-carboxylic acid phenylamide (6bo)

Using general procedure 3, 2-aminocycloalkylthiophene (5b) (100 mg, 0.349 mmol) was reacted with chloroacetyl chloride to generate the title compound (6bo) as white solid (22 mg, 16%). $^1$H NMR (500 MHz, CDCl$_3$) δ 1.14-1.78 (m, 4H), 1.93-1.95 (m, 2H), 2.82-2.84 (m, 2H), 2.97-2.99 (m, 2H), 7.21 (t, J=8 Hz, 1H), 7.32 (bs, 1H), 7.41 (t, J=8 Hz, 2H), 7.55 (d, J=8 Hz), 11.98 (bs, 1H). ESI-LCMS (low resolution) m/z calculated for $C_{18}H_{17}ClF_2N_2O_2S$ [M+H] 399.1, found [M+H] 399.0.

Example 42

2-(2-Bromo-2,2-difluoro-acetylamino)-5,6,7,8-tetrahydro-4H-cyclohepta[b]thiophene-3-carboxylic acid phenylamide (6 bp)

Using general procedure 3, 2-aminocycloalkylthiophene (5b) (100 mg, 0.349 mmol) was reacted with bromoacetyl chloride to generate the title compound (6 bp) as a white powder (24 mg, 17%). $^1$H NMR (500 MHz, CDCl$_3$) δ 1.74-1.78 (m, 4H), 1.92-1.95 (m, 2H), 2.82-2.84 (m, 2H), 2.97-2.99 (m, 2H), 7.21 (t, J=8 Hz, 1H), 7.32 (bs, 1H), 7.41 (t, J=8 Hz, 2H), 7.55 (d, J=8 Hz, 2H), 11.94 (bs, 1H). ESI-LCMS (low resolution) m/z calculated for $C_{18}H_{17}BrF_2N_2O_2S$ [M+H] 444.3, found [M+H] 444.2.

Example 43

2-(2,2-Difluoro-2-iodo-acetylamino)-5,6,7,8-tetrahydro-4H-cyclohepta[b]thiophene-3-carboxylic acid phenylamide (6bq)

Using general procedure 4, 2-aminocycloalkylthiophene (5b) (218 mg, 0.761 mmol) was reacted with difluoroiodoacetic acid to generate the title compound (6bq) after column chromatography (gradient of hexane and ethyl acetate) as an off-white solid (50 mg, 13%). $^1$H NMR (500 MHz, CDCl$_3$) δ 1.71-1.80 (m, 4H), 1.89-1.96 (m, 2H), 2.83 (t, 2H, J=5 Hz), 2.97 (t, 2H, J=5 Hz), 7.21 (t, 1H, J=8 Hz), 7.31 (s, 1H), 7.41 (t, 2H, J=8 Hz), 7.56 (d, 2H, J=8 Hz), 11.84 (s, 1H). ESI-LCMS (low resolution) m/z calculated for C$_{18}$H$_{17}$F$_2$IN$_2$O$_2$S [M+H] 491.3, found [M+H] 491.3.

Example 44

2-(2-Chloro-2,2-difluoro-acetylamino)-5,6,7,8-tetrahydro-4H-cyclohepta[b]thiophene-3-carboxylic acid (4-fluoro-phenyl)-amide (6br)

Using general procedure 3, 2-aminocycloalkylthiophene (5e) (70 mg, 0.230 mmol) was reacted with chloroacetyl chloride to generate the title compound (6br) as a red solid (18 mg, 19%). $^1$H NMR (500 MHz, CDCl$_3$) δ 1.56-1.58 (m, 2H), 1.76-1.78 (m, 2H), 1.92-1.93 (m, 2H), 2.80-2.82 (m, 2H), 2.96-2.98 (m, 2H), 7.06-7.10 (m, 2H), 7.29 (bs, 1H), 7.51-7.54 (m, 2H), 11.96 (bs, 1H), ESI-LCMS (low resolution) m/z calculated for C$_{18}$H$_{16}$ClF$_3$N$_2$O$_2$S [M+H] 417.8, found [M+H] 417.9.

Example 45

2-(2-Bromo-2,2-difluoro-acetylamino)-5,6,7,8-tetrahydro-4H-cyclohepta[b]thiophene-3-carboxylic acid (4-fluoro-phenyl)-amide (6bs)

Using general procedure 3, 2-aminocycloalkylthiophene (5e) (50 mg, 0.164 mmol) was reacted with bromoacetyl chloride to generate the title compound (6bs) as a yellow solid (24 mg, 32%). $^1$H NMR (500 MHz, CDCl$_3$) δ 1.74-1.77 (m, 4H), 1.91-1.93 (m, 2H), 2.91-2.83 (m, 2H), 2.96-2.98 (m, 2H), 7.10 (t, J=9 Hz, 2H), 7.32 (bs, 1H), 7.52-7.54 (m, 2H), 11.92 (bs, 1H). ESI-HRMS m/z calculated for C$_{18}$H$_{16}$BrF$_3$N$_2$O$_2$S [M–H] 458.9995, found [M–H] 458.9994.

Example 46

2-(2,2-Difluoro-2-iodo-acetylamino)-5,6,7,8-tetrahydro-4H-cyclohepta[b]thiophene-3-carboxylic acid (4-fluoro-phenyl)-amide (6bt)

Using general procedure 4, 2-aminocycloalkylthiophene (5e) (100 mg, 0.329 mmol) was reacted with difluoroiodoacetic acid to generate the title compound (6bt) as an off-white solid (143 mg, 86%). $^1$H NMR (500 MHz, CDCl$_3$) δ 1.75-1.79 (m, 4H), 1.91-1.95 (m, 2H), 2.80-2.85 (m, 2H), 2.94-3.01 (m, 2H), 7.08-7.11 (m, 2H), 7.51-7.53 (m, 2H), 11.83 (bs, 1H). $^{13}$C NMR (125 MHz, CDCl$_3$) δ 27.1, 27.5, 28.8, 29.1, 31.6, 89.5, 116.0 (d, J=92 Hz), 120.2, 122.6 (d, J=32 Hz), 132.8, 133.2, 134.9, 139.0, 157.7, 158.9, 160.9, 164.2. ESI-HRMS m/z calculated for C$_{18}$H$_{16}$F$_3$IN$_2$O$_2$S [M–H] 506.9856, found [M–H] 506.9852.

Example 47

2-(2-Chloro-2,2-difluoro-acetylamino)-5,6-dihydro-4H-cyclopenta[b]thiophene-3-carboxylic acid (2-trifluoromethoxy-phenyl)-amide (6bu)

Using general procedure 3, 2-aminocycloalkylthiophene (5v) (70 mg, 0.204 mmol) was reacted with chloroacetyl chloride to generate the title compound (6bu) as a white solid (75 mg, 81%). $^1$H NMR (500 MHz, CDCl$_3$) δ 2.62 (p, J=7 Hz, 2H), 2.99 (t, J=7 Hz, 2H), 3.10 (t, J=7 Hz, 2H), 7.18 (d, J=8 Hz, 1H), 7.37-7.38 (m, 2H), 8.18 (bs, 1H), 8.58 (d, J=8 Hz, 1H), 13.01 (bs, 1H). $^{13}$C NMR (125 MHz, CDCl$_3$) δ 28.4, 28.7, 29.5, 113.1, 118.7, 120.1, 122.0, 124.8, 127.7, 129.9, 136.0, 137.4, 138.3, 148.2, 163.5. ESI-HRMS m/z calculated for C$_{17}$H$_{12}$ClF$_5$N$_2$O$_3$S [M–H] 453.0104, found [M–H] 453.0103.

Example 48

2-(2-Bromo-2,2-difluoro-acetylamino)-5,6-dihydro-4H-cyclopenta[b]thiophene-3-carboxylic acid (4-methyl-2-trifluoromethoxy-phenyl)-amide (6bv)

Using general procedure 3, 2-aminocycloalkylthiophene (5v) (50 mg, 0.146 mmol) was reacted with bromoacetyl chloride to generate the title compound (6bv) as a brown solid (29 mg, 40%). $^1$H NMR (500 MHz, CDCl$_3$) δ 2.60-2.63 (m, 2H), 2.98 (t, J=8 Hz, 2H), 3.09 (t, J=8 Hz, 2H), 7.18 (d, J=8 Hz, 1H), 7.35-7.38 (m, 2H), 8.17 (bs, 1H), 8.57 (d, J=8 Hz, 1H), 12.96 (bs, 1H). $^{13}$C NMR (125 MHz, CDCl$_3$) δ 28.4, 28.7, 29.5, 111.0, 113.1, 119.6, 120.1, 122.0, 124.8, 127.7, 129.9, 136.1, 137.4, 138.3, 148.2, 156.3 (q, J=32 Hz), 163.5. ESI-HRMS m/z calculated for C$_{17}$H$_{12}$BrF$_5$N$_2$O$_3$S [M–H] 496.9599, found [M–H] 496.9598.

Example 49

2-(2,2-Difluoro-2-iodo-acetylamino)-5,6-dihydro-4H-cyclopenta[b]thiophene-3-carboxylic add (2-trifluoromethoxy-phenyl)-amide (6bw)

Using general procedure 4, 2-aminocycloalkylthiophene (5v) (57.0 mg, 0.167 mmol) was reacted with difluoroiodoacetic acid to generate the title compound (6bw) as an off-white solid (45.3 mg, 52%). $^1$H NMR (500 MHz, CDCl$_3$) δ 2.61 (m, 2H), 2.98 (t, 2H, J=7.5 Hz), 3.09 (t, 2H, J=7.5 Hz), 7.18 (td, 1H, J=9, 2 Hz), 7.29-7.40 (m, 2H), 8.17 (s, 1H), 8.58 (dd, 1H, J=9, 2 Hz). $^{13}$C NMR (125 MHz, CDCl$_3$) δ 28.4, 28.7, 29.5, 89.5, 113.1, 120.0, 121.6, 121.9, 124.7, 127.6, 129.9, 135.9, 137.4, 138.3, 148.2, 159.7, 163.5. ESI-HRMS m/z calculated for C$_{17}$H$_{12}$F$_5$IN$_2$O$_3$S [M–H] 544.9461, found [M–H] 544.9457.

Example 50

N-(5-chloro-2-methoxyphenyl)-2-(2,2,2-trifluoroacetamido)-5,6,7,8-tetrahydro-4H-cyclohepta[b]thiophene-3-carboxamide (am1_47) was Prepared According to the General Procedure 3 as Disclosed Herein

Example 51

TMEM16A Inhibition

Cell lines and culture. Fischer Rat Thyroid (FRT) cells stably co-expressing TMEM16A, TMEM16B and human wild-type CFTR and the halide-sensitive yellow fluorescent protein (YFP)-H148Q were cultured as described. (See Namkung, W. et al., *J Biol Chem* 2011, 286, (3), 2365-74) HT-29 expressing YFP were cultured as described. (See De La Fuente, R. et al., *Mol Pharmacol* 2008, 73, (3), 758-68.) FRT cells were cultured on plastic in Coon's-modified Ham's F12 medium supplemented with 10% fetal bovine serum, 2 mM L-glutamine, 100 units/mL penicillin, and 100 µg/mL streptomycin. For plate reader assays, cells were plated in black 96-well microplates (Corning-Costar Corp., New York, N.Y.) at a density of 20,000 cells per well and assayed 24-48 hours after plating.

TMEM16A functional assay. TMEM16A functional plate-reader assay was done as previously described. (See Namkung, W. et al., *J Biol Chem* 2011, 286, (3), 2365-74.) Briefly, each well of 96-well plate containing the TMEM16A-expressing FRT cells was washed twice with phosphate buffer saline (PBS) leaving 50 µl. Test compounds (0.5 µl in DMSO) were added to each well at specified concentration. After 10 min each well was assayed individually for TMEM16A-mediated I$^-$ influx by recording fluorescence continuously (400 ms/point) for 2 s (baseline), then 50 µl of 140 mM I$^-$ solution containing 300 µM ATP was added at 2 s, and fluorescence was further read for 12 s. The initial rate of I– influx following each of the solution additions was computed from fluorescence data by nonlinear regression. TMEM16B activity was assayed similarly as described using FRT cells co-expressing YFP and TMEM16B. (See Namkung, W. et al., *J Biol. Chem* 2011, 286, (3), 2365-74.)

Short-circuit current measurement. Short-circuit current measurements were done as described. (See Piechowicz, K. A. et al., *J Enzyme Inhib Med Chem* 2016, 1-7.) Briefly, Snapwell inserts (Corning Costar, Corning, N.Y.) containing TMEM16A-expressing FRT cells were mounted in Ussing chambers (Physiological instruments, San Diego, Calif.). The hemichambers were filled with 5 ml of $HCO_3^-$ buffered solution (basolateral) and half-Cl$^-$ solution (apical), and the basolateral membrane was permeabilized with 250 µg/ml amphotericin B. Solutions were bubbled with 95% $O_2$/5% $CO_2$ and maintained at 37° C., and short-circuit current was measured on a DVC-1000 voltage clamp (World Precision Instruments Inc., Sarasota, Fla.) using Ag/AgCl electrodes and 3 M KCl agar bridges.

Concentration-dependence for selected compounds is shown in FIG. 2, with $IC_{50}$ values summarized in Table 4. By short-circuit current assay, 6aa showed an $IC_{50}$ of 0.26 µM, similar to the chlorodifluoroacetamide 6bk with $IC_{50}$ of 0.23 µM. Difluoroiodoacetamides 6bn and 6bt were less potent with $IC_{50}$ of 0.73 and 0.60 µM, respectively. Notably, bromodifluoroacetamide 6bm had $IC_{50}$ of 0.030 µM.

Example 52

In Vitro Metabolic Stability

Compounds (each 10 uM) were incubated for specific time points (2, 5, 15, 30, 60, 180 min) with shaking at 37° C. with rat liver microsomes (1 mg protein/mL, Sigma-Aldrich, St. Louis, Mo.) in potassium phosphate butler (100 mM) containing 1 mM NADPH. The mixture was then chilled on ice, and 0.5 mL of ice-cold ethyl acetate was added. Samples were centrifuged for 15 min at 3000 RPM. The supernatant was evaporated to dryness, and the residue was dissolved in 80 µL of mobile phase (acetonitrile:/water, 3:1, containing 0.1% formic acid) for LC/MS. Reverse-phase HPLC separation was carried out using a Waters $C_{18}$ column (2.1 mm×100 mm, 3.5 mm particle size) equipped with a solvent delivery system (Waters model 2690, Milford, Mass.). The solvent system consisted of a linear gradient from 5% to 95% acetonitrile run over 16 min (0.2 mL/min flow rate).

Plate reader assays of chloride channel function, CFTR inhibition was assayed as described. (See Tradtrantip, L., *J Med Chem* 2009, 52, (20), 6447-55.) Briefly, FRT cells co-expressing YFP and wildtype CFTR were washed with phosphate-buffered saline (PBS) and then incubated for 15 min with test compounds in PBS containing 20 µM forskolin. I$^-$ influx was measured in a plate reader with initial baseline read for 2 s and then for 12 s after rapid addition of an I$^-$ containing solution. Activity of non-TMEM16A CaCC was assayed as described in HT-29 cells expressing YFP. (See De La Fuente, R. et al., *Mol Pharmacol* 2008, 73, (3), 758-68.) In each assay initial rates of I– influx were computed as a linear measure of channel function.

Cytotoxicity. FRT cells were cultured overnight in black 96-well Costar microplates and incubated with 5 µM test compounds for 8 h. Cytotoxicity was measured by Alamar Blue assay (Invitrogen, Carlsbad, Calif.) as per the manufacturer's instructions.

FIG. 3C summarizes the time course of compound degradation showing remarkably greater stability of 6bm compared to Ani-9. 6bm could be potentially metabolized by amide-bond hydrolysis or oxidation of the benzene or aryl methyl. It is speculated that Ani-9 could be oxidized at the aryl methyl or N—N bond; or hydrolyzed at the amide or hydrazone linkages.

Example 53

Ex Vivo Intestinal Contractility

The effect of a compound according to one embodiment on intestinal contractility was determined in an ex vivo preparation of mouse ileum. Adult mice (CD1 genetic background) were euthanized by avertin overdose (200 mg/kg, 2,2,2-tribromethanol, Sigma-Aldrich) and ileal segments of ~2 cm length were isolated and washed with Krebs-Henseleit buffer (pH 7.4, in mM: 118 NaCl, 4.7 KCl, 1.2 $MgSO_4$, 1.2 $KH_2PO_4$, 25 $NaHCO_3$, 2.5 $CaCl_2$, 11 D-glucose). The ends of the ileal segments were tied, connected to a force transducer (Biopac Systems, Goleta, Calif.) and tissues were transferred to an organ chamber (Biopac Systems) containing Krebs-Henseleit buffer at 37° C. aerated with 95% $O_2$, 5% $CO_2$. Tissues were stabilized for 60 min with resting tension of 0.5 g and solutions were changed every 15 min. Effects of 6bm on baseline isometric intestinal contractions were recorded. As is shown in FIG. 4, 6bm strongly inhibited spontaneous isometric contractions of ileum in a concentration-dependent manner.

Example 54

Inhibition Study of Tumor Cell Lines

Compounds according to the present disclosure (structures shown in FIG. 5B) were tested for their inhibitory effect on proliferation of SW-480 cell line.

SW-480 cells were cultured on plastic in Leibovitz L15 medium supplemented with 10% fetal bovine serum, 2 mM L-glutamine, 100 units/mL penicillin, and 100 µg/mL streptomycin. The cells were incubated at 37° C. without $CO_2$.

SW-480 cells were plated into black 96-well microplates (Corning-Costar Corp., New York, N.Y.) at 10% seeding. The cells were treated with test compounds dissolved in DMSO in serial dilution while maintaining the final concentration of DMSO at 0.5%. Plated cells were then incubated for 72 h at 37° C. Cell proliferation was quantified using the AlamarBlue assay (Invitrogen, Carlsbad, Calif.) as per the manufacturer's instructions. Data was normalized against untreated control cells that were lysed for 10 minutes using Triton-X100 (0.1% in PBS).

Figure 5A:
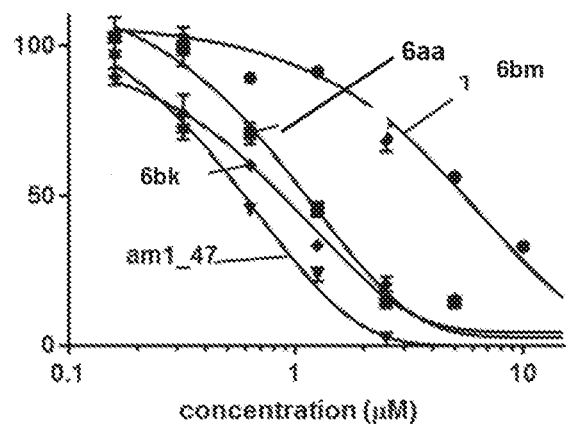
FIGS. 5A and 5B show AACT compounds inhibit proliferation of SW-480 adenocarcinoma cells.
Figure 5B:
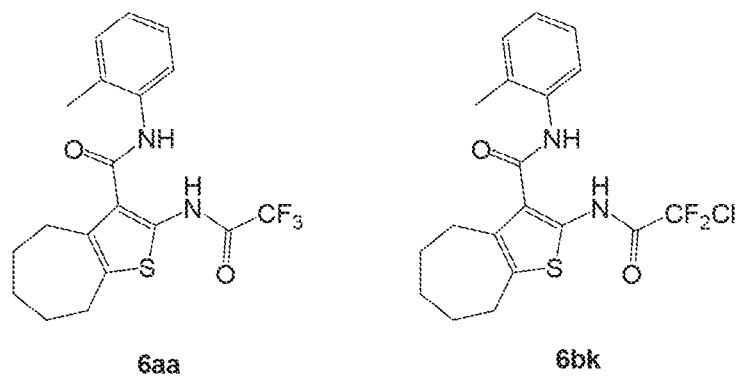
Figure 5B:
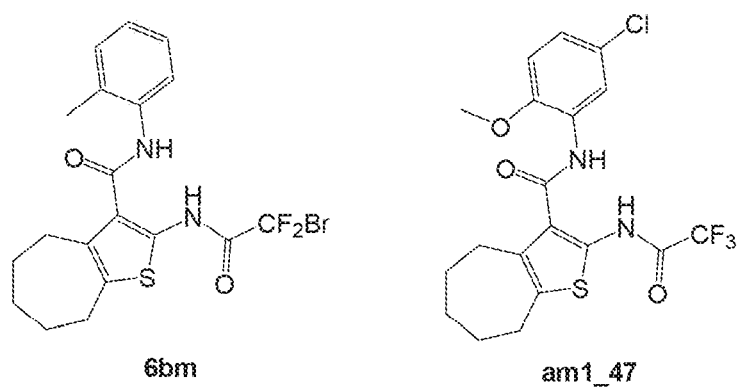

FIG. 5A shows compound concentration-dependent inhibition of cell proliferation as assayed by AlamarBlue after 72 h of drug treatment. Compound am1_47 (i.e., N-(5-chloro-2-methoxyphenyl)-2-(2,2,2-trifluoroacetamido)-5,6,7,8-tetrahydro-4H-cyclohepta[b]thiophene-3-carboxamide) was the most potent, with an $IC_{50}$ of 0.47 μM. Less potent inhibitors included 6bk ($IC_{50}$=0.75 μM); 6aa ($IC_{50}$=0.95 μM); and 6bm ($IC_{50}$=7 μM).

Compound am1_47 was shown as considerably more potent than $CaCC_{inh}$-A01 (6-t-butyl-2-(furan-2-carboxamido)-4,5,6,7-tetrahydrobenzo[b] thiophene-3-carboxylic acid) in inhibiting proliferation of SW480 cells. The compound $CaCC_{inh}$-A01 has been reported to inhibit proliferation of several types of TMEM16A-expressing tumor cell lines, including SW480, albeit at relatively high concentrations (10-20 μM).

Example 55

Pharmacokinetic Studies

The pharmacokinetics of compounds according to certain embodiments was studied in rats. Rats (Wistar males, 250-300 g) were purchased from Charles River Laboratories (Wilmington, Mass.) and were treated with 4 mg/kg 6bm (in 5% DMSO, 10% Kolliphor HS in saline) either intraperitoneally or by oral gavage. After treatments blood samples were collected by tail vein puncture at specified time points (15, 30, 60, 120 and 180 min). Serum was separated by centrifuging blood samples at 5000 rpm for 15 min. 6bm concentration were quantified as follows; A 190 μL aliquot plasma, containing different concentrations of bromodifluoroacetyl compound 6bm, was spiked with 10 μL of the chlorodifluoroacetyl-containing internal standard 6bk. The aliquot was then diluted to a total of 2 mL in PBS. A $C_{18}$ solid-phase extraction (SPE) column (Thermo Fisher, Waltham, Mass.) was conditioned with methanol (2 mL) and PBS (2 mL). The aliquot was loaded onto the conditioned SPE column, and washed with PBS (2 mL) followed by water (2 mL), and the column then dried under vacuum for 5 min. Analytes were eluted with ethyl acetate (3 mL), and concentrated by rotary evaporation. The residues were reconstituted into methanol (150 μL), and then analyzed using a hybrid quadrupole Q-Exactive Orbitrap mass analyzer (Thermo Fisher, Waltham, Mass.), with an electrospray ionization source, employing parallel-reaction monitoring (PRM) to provide high analytical sensitivity.

Intraperitoneal administration of 6bm at 4 mg/kg yielded serum concentrations greater than 3.5 μM for up to 2 h (peak 6.5 μM at 60 min); while oral administration at the same dose produced serum concentrations greater than 0.5 μM for 3 h (peak 1.9 μM at 2 h). Both administration methods produced serum concentrations well above the $IC_{50}$ of 6bm (30 nM) for inhibition of TMEM16A. No toxic effect was seen.

Figure 6:
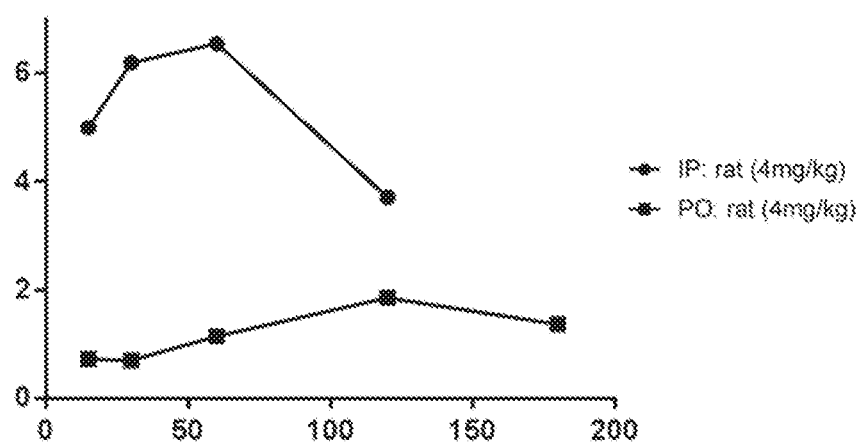
FIG. 6 shows AACT compound 6bm is detectable at pharmacologically relevant concentrations after intraperitoneal (IP) or oral administration (PO).

FIG. 6 shows that compound 6bm is detectable at pharmacologically relevant concentrations after intraperitoneal (IP) or oral administration (PO).

Example 56

Hypertension Indication

TMEM16A is expressed in vascular smooth muscle and its inhibition may reduce blood pressure. In a proof of concept study, AACT inhibitor 6bm was administered acutely to rats made hypertensive with phenylephrine. More specifically, a wild-type anesthetized rat was made hypertensive with intravenous (IV) phenylephrine (PE, 0.25 mg) and then administered IV vehicle (Veh, 5% DMSO-10% Kolliphor HS in saline) and then 0.3 mg 6bm (IV, in vehicle). Blood pressure was measured by femoral artery catheter.

Figure 7:
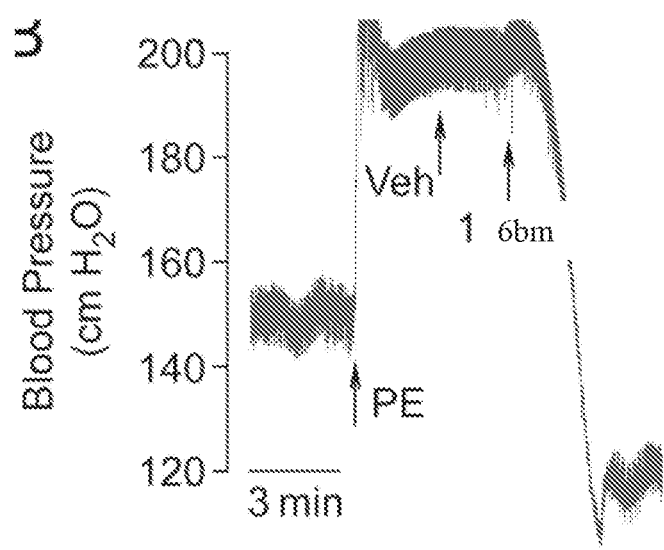
FIG. 7 shows acute reduction in blood pressure (measured by femoral artery catheter) in a wild-type anesthetized rat made hypertensive with intravenous (IV) phenylephrine (PE, 0.25 mg) and then administered IV vehicle (Veh, 5% DMSO-10% Kolliphor HS in saline) and then 0.3 mg compound 6bm (IV, in vehicle).

As shown in FIG. 7, the compound 6bm demonstrated acute reduction in blood pressure, indicating that the compounds according to the present disclosure can be suitable for treating hypertension.

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference, in their entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having one of the following structures (I-5), (I-6) or (I'-6)

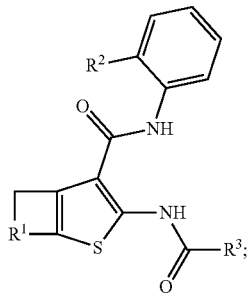

(I-5)

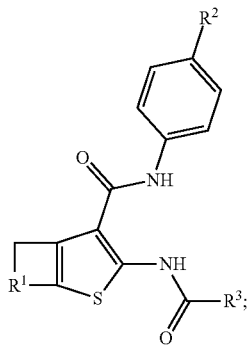

(I-6)

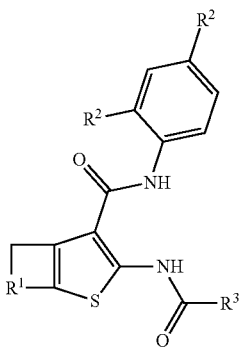

or a pharmaceutically acceptable salt, isotopic form, stereoisomer or prodrug thereof, wherein:

$R^1$ is optionally substituted $C_1$-$C_6$ alkylene or optionally substituted heteroalkylene;

each $R^2$ is the same or different and independently hydrogen, methyl, ethyl, $C_1$-$C_6$ alkoxy, $C_1$-$C_6$ haloalkyl, or $C_1$-$C_6$ haloalkoxy; and $R^3$ is $C_1$-$C_6$ haloalkyl having at least two different halogens.

2. The compound of claim 1, having one of the following structures (I-7), (I-8) or (I'-8):

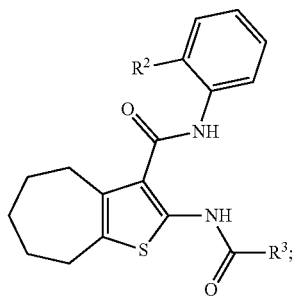

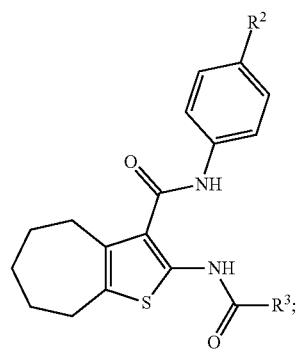

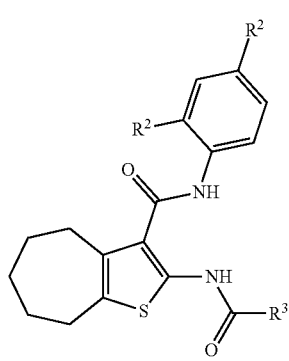

wherein:

each $R^2$ is independently H, methyl, ethyl, $C_1$-$C_6$ alkoxy, $C_1$-$C_6$ haloalkyl, or $C_1$-$C_6$ haloalkoxy; and $R^3$ is $C_1$-$C_6$ haloalkyl having at least two different halogens.

3. The compound of claim 1 being:
2-(2-chloro-2,2-difluoro-acetylamino)-5,6,7,8-tetrahydro-4H-cyclohepta[b]thiophene-3-carboxylic acid o-tolylamide;
2-(2-bromo-2,2-difluoro-acetylamino)-5,6,7,8-tetrahydro-4H-cyclohepta[b]thiophene-3-carboxylic acid o-tolylamide;
2-(2,2-Difluoro-2-iodo-acetylamino)-4H-cyclohepta[b]thiophene-3-carboxylic acid o-tolylamide;
2-(2-chloro-2,2-difluoro-acetylamino)-5,6,7,8-tetrahydro-4H-cyclohepta[b]thiophene-3-carboxylic acid phenylamide;
2-(2-bromo-2,2-difluoro-acetylamino)-5,6,7,8-tetrahydro-4H-cyclohepta[b]thiophene-3-carboxylic acid phenylamide; or
2-(2,2-difluoro-2-iodo-acetylamino)-5,6,7,8-tetrahydro-4H-cyclohepta[b]thiophene-3-carboxylic acid phenylamide.

4. The compound of claim 1 wherein $R^2$ is H, methyl, ethyl, trifluoromethyl, or trifluoromethoxy.

5. The compound of claim 4, wherein $R^3$ is perhaloalkyl.

6. The compound of claim 5 wherein $R^3$ is chlorodifluoromethyl, bromodifluoromethyl, or difluoroiodomethyl.

7. A pharmaceutical composition comprising a physiologically acceptable excipient and a compound of claim 1.

8. The pharmaceutical composition of claim 7 wherein the compound of Formula (I) is:
2-(2-chloro-2,2-difluoro-acetylamino)-5,6,7,8-tetrahydro-4H-cyclohepta[b]thiophene-3-carboxylic acid o-tolylamide;
2-(2-bromo-2,2-difluoro-acetylamino)-5,6,7,8-tetrahydro-4H-cyclohepta[b]thiophene-3-carboxylic acid o-tolylamide;
2-(2,2-Difluoro-2-iodo-acetylamino)-5,6,7,8-tetrahydro-4H-cyclohepta[b]thiophene-3-carboxylic acid o-tolylamide;
2-(2-chloro-2,2-difluoro-acetylamino)-5,6,7,8-tetrahydro-4H-cyclohepta[b]thiophene-3-carboxylic acid phenylamide;
2-(2-bromo-2,2-difluoro-acetylamino)-5,6,7,8-tetrahydro-4H-cyclohepta[b]thiophene-3-carboxylic acid phenylamide; or
2-(2,2-difluoro-2-iodo-acetylamino)-5,6,7,8-tetrahydro-4H-cyclohepta[b]thiophene-3-carboxylic acid phenylamide.

9. A compound selected from the group consisting of:
2-(2-chloro-2,2-difluoro-acetylamino)-5,6,7,8-tetrahydro-4H-cyclohepta[b]thiophene-3-carboxylic acid (4-fluoro-phenyl)-amide;
2-(2-bromo-2,2-difluoro-acetylamino)-5,6,7,8-tetrahydro-4H-cyclohepta[b]thiophene-3-carboxylic acid (4-fluoro-phenyl)-amide; and
2-(2,2-difluoro-2-iodo-acetylamino)-5,6,7,8-tetrahydro-4H-cyclohepta[b]thiophene-3-carboxylic acid (4-fluoro-phenyl)-amide.

* * * * *